(12) United States Patent
Monaco

(10) Patent No.: US 12,337,684 B2
(45) Date of Patent: Jun. 24, 2025

(54) METHOD AND COMPUTING SYSTEM FOR MITIGATING MOTION SICKNESS IN A VEHICLE

(71) Applicant: Mercedes-Benz Group AG, Stuttgart (DE)

(72) Inventor: Christopher Monaco, Sunnyvale, CA (US)

(73) Assignee: Mercedes-Benz Group AG, Stuttgart (DE)

( * ) Notice: Subject to any disclaimer, the term of this patent is extended or adjusted under 35 U.S.C. 154(b) by 283 days.

(21) Appl. No.: 18/190,447

(22) Filed: Mar. 27, 2023

(65) Prior Publication Data

US 2024/0326591 A1 Oct. 3, 2024

(51) Int. Cl.
*B60K 35/00* (2024.01)
*B60K 35/22* (2024.01)
*B60K 35/28* (2024.01)
*B60K 35/65* (2024.01)

(52) U.S. Cl.
CPC ............. *B60K 35/00* (2013.01); *B60K 35/22* (2024.01); *B60K 35/28* (2024.01); *B60K 35/65* (2024.01); *B60K 2360/167* (2024.01); *B60K 2360/175* (2024.01); *B60K 2360/33* (2024.01)

(58) Field of Classification Search
None
See application file for complete search history.

(56) References Cited

U.S. PATENT DOCUMENTS

| 10,053,226 | B2 | 8/2018 | Leland |
| 10,926,773 | B2 | 2/2021 | Vulcu |
| 11,175,522 | B2 | 11/2021 | Peso et al. |
| 11,321,923 | B2 | 5/2022 | Rober et al. |
| 11,619,489 | B2* | 4/2023 | Ziebart ................. B60K 37/20 340/440 |
| 2015/0097861 | A1 | 4/2015 | Alaniz et al. |
| 2017/0254524 | A1* | 9/2017 | Bergman ............... H05B 47/10 |
| 2017/0291538 | A1* | 10/2017 | Sivak .................. A61N 5/0618 |

(Continued)

FOREIGN PATENT DOCUMENTS

| DE | 102019208315 B4 | 6/2022 |
| WO | 2017/176920 A1 | 10/2017 |
| WO | WO 2021/213907 A1 | 10/2021 |

OTHER PUBLICATIONS

Scholz Hubert, Display Device For A Motor Vehicle With An Elongated Display Device For Displaying Optically Moving Information, As Well As A Motor Vehicle, Jan. 14, 2021 (Year: 2021).*

(Continued)

*Primary Examiner* — James J Lee
*Assistant Examiner* — Andrew Sang Kim
(74) *Attorney, Agent, or Firm* — Dority & Manning, P.A.

(57) ABSTRACT

Methods and computing systems for mitigating motion sickness are described. A computing system includes a control circuit to receive data indicating an inertial state of a vehicle, simulate a fluid based on the data indicating the inertial state of the vehicle, and output command instructions to cause the simulated fluid to be visualized within an interior of the vehicle using one or more lighting elements from among a plurality of activatable lighting elements of the vehicle.

18 Claims, 14 Drawing Sheets

(56) References Cited

U.S. PATENT DOCUMENTS

2020/0331386 A1 10/2020 Szczerba et al.
2020/0384240 A1* 12/2020 Linder .................. A61M 21/02

OTHER PUBLICATIONS

Healthline, "Can Motion Sickness Glasses Stop You from Feeling Ill?", Jul. 28, 2020, https://www.healthline.com/health/glasses-for-motion-sickness#bottom-line, retrieved Feb. 9, 2023, 5 pages.

Abhraneil Dam et al., "A Review of Motion Sickness in Automated Vehicles", Proceedings of the 7th ACM Conference on Information—Centric Networking, ACMPUB27, New York, NY, USA, Sep. 9, 2021, pp. 39-48, XP058623323.

Alexander Meschtscherjakov et al., "Bubble Margin: Motion Sickness Prevention While Reading on Smartphones in Vehicles", Center for Human-Computer Interaction, University of Salzburg, Salzburg, Austria, Sep. 6, 2019, 19 pages, XP093172008, Retrieved from the Internet: URL:https://inria.hal.science/hal-02544623v1/preview/488591_1_En_39_Chapter.pdf#page=2 [retrieved on Jun. 5, 2024].

International Search Report with Written Opinion of the International Searching Authority for the Application No. PCT/EP2024/025115 mailed Jun. 26, 2024.

* cited by examiner

METHOD AND COMPUTING SYSTEM FOR MITIGATING MOTION SICKNESS IN A VEHICLE

FIELD

The disclosure relates generally to methods and systems for mitigating motion sickness of an occupant in a vehicle. More particularly, the disclosure relates generally to methods and systems for simulating a fluid based on data indicating an inertial state of the vehicle and visualizing the simulated fluid within an interior of the vehicle using one or more lighting elements of the vehicle.

BACKGROUND

Motion sickness occurs when the movement a person sees is different from what their inner ear senses. Motion sickness can cause dizziness, nausea, and vomiting. For example, motion sickness can occur when an occupant is in a vehicle (e.g., a car, a train, an airplane, a boat, etc.). Occurrences of motion sickness in automobiles is likely to increase based on current automotive trends. For example, windows for many vehicles produced recently have been reduced in size due to various design considerations. The reduced window size also reduces the number of visual motion cues within a field of view of occupants of a vehicle, increasing the likelihood of motion sickness. Furthermore, as vehicles include additional infotainment features and automated driving capabilities, drivers and passengers will likely spend more time focusing on activities within the vehicle itself.

SUMMARY

Aspects and advantages of embodiments of the disclosure will be set forth in part in the following description, or may be learned from the description, or may be learned through practice of the embodiments.

One example aspect of the disclosure is directed to a computing system. The computing system may include a control circuit configured to perform operations. The operations may include receiving data indicating an inertial state of a vehicle, simulating a fluid based on the data indicating the inertial state of the vehicle, and outputting command instructions to cause the simulated fluid to be visualized within an interior of the vehicle using one or more lighting elements from among a plurality of activatable lighting elements of the vehicle.

In an embodiment, the control circuit is configured to model fluid dynamics associated with the fluid based on the data indicating the inertial state of the vehicle to simulate the fluid based on the data indicating the inertial state of the vehicle.

In an embodiment, the control circuit is configured to determine the one or more lighting elements from among the plurality of activatable lighting elements to be selectively deactivated, activated, or both, to simulate the fluid based on the data indicating the inertial state of the vehicle.

In an embodiment, to output the command instructions to cause the simulated fluid to be visualized within the interior of the vehicle the control circuit is configured to output the command instructions to activate, deactivate, or both, the one or more lighting elements from among the plurality of activatable lighting elements to visualize the simulated fluid within the interior of the vehicle.

In an embodiment, the control circuit is further configured to receive a first input to execute a motion sickness mitigation application. In response to executing the motion sickness mitigation application, the control circuit is further configured to receive a second input identifying a respective location of one or more occupants within the vehicle or a zone within the vehicle, and determine the one or more lighting elements from among the plurality of activatable lighting elements to visualize the simulated fluid based on the second input.

In an embodiment, the control circuit is further configured to receive data indicating a location of an occupant within the vehicle and determine the one or more lighting elements from among the plurality of activatable lighting elements to visualize the simulated fluid based on the location of the occupant such that the visualization of the simulated fluid is in a field of view of the occupant.

In an embodiment, the plurality of activatable lighting elements are provided at, at least one of: (i) a dashboard of the vehicle, (ii) one or more seats of the vehicle, (iii) one or more door panels of the vehicle, (iv) one or more display screens of the vehicle, (v) one or more windows of the vehicle, or (vi) one or more consoles of the vehicle.

In an embodiment, the plurality of activatable lighting elements are provided in an array, and the command instructions are configured to deactivate, activate, or both, the one or more lighting elements of the plurality of activatable lighting elements provided in the array to visualize the simulated fluid.

In an embodiment, the control circuit is further configured to determine at least one of a linear acceleration or an angular velocity of the vehicle based on the data indicating the inertial state of the vehicle, and simulate the fluid based on at least one of the linear acceleration or the angular velocity of the vehicle.

In an embodiment, to simulate the fluid the control circuit is configured to determine movement of suspended air bubbles in the fluid based on the data indicating the inertial state of the vehicle, and the command instructions are configured to cause the one or more lighting elements from among the plurality of activatable lighting elements to be controlled to visualize the movement of the suspended air bubbles in the fluid based on the inertial state of the vehicle.

In an embodiment, as the vehicle turns in a first direction, the command instructions are configured to deactivate, activate, or both, a first subset of the plurality of activatable lighting elements to visualize the simulated fluid, based on how a linear velocity and angular orientation of the vehicle changes over time based on the inertial state, and as the vehicle turns in a second direction, the command instructions are configured to deactivate, activate, or both, a second subset of the plurality of activatable lighting elements to visualize the simulated fluid, based on how the linear velocity and angular orientation of the vehicle changes over time based on the inertial state.

In an embodiment, the control circuit is configured to receive the data indicating the inertial state of the vehicle from at least one of: (i) one or more accelerometers, (ii) one or more gyroscopes, (iii) one or more magnetometers, (iv) one or more inclinometers, (v) one or more cameras, (vi) one or more LIDAR sensors, (vii) one or more RADAR sensors, (viii) one or more wheel speed sensors, or (ix) one or more global navigation positioning sensors.

In an embodiment, the data indicating the inertial state of the vehicle includes at least one of: (i) acceleration data of the vehicle, (ii) angular motion data of the vehicle, (iii) speed data of the vehicle, (iv) pitch angle data of the vehicle, (v) roll angle data of the vehicle, or (vi) yaw angle data of the vehicle.

In an embodiment, the control circuit is configured to determine, based on a default setting or a user setting, a viscosity of the fluid to model the fluid dynamics associated with the fluid. The simulated fluid may be based on the viscosity of the fluid.

In an embodiment, the simulated fluid includes a simulation of the fluid itself and a simulation of one or more objects in the fluid, the one or more objects including one or more of: (i) granules, (ii) air bubbles, (iii) filaments, or (iv) fiber-like structures.

Another example aspect of the disclosure is directed to a computer-implemented method. The computer-implemented method may include receiving data indicating an inertial state of a vehicle, simulating a fluid based on the data indicating the inertial state of the vehicle, and outputting command instructions to cause the simulated fluid to be visualized within an interior of the vehicle using one or more lighting elements from among a plurality of activatable lighting elements of the vehicle.

In an embodiment, simulating the fluid based on the data indicating the inertial state of the vehicle includes modeling fluid dynamics associated with the fluid and one or more objects in the fluid according to the inertial state of the vehicle.

In an embodiment, the vehicle is an autonomous vehicle.

In an embodiment, simulating the fluid based on the data indicating the inertial state of the vehicle comprises determining the one or more lighting elements from among the plurality of activatable lighting elements to be selectively deactivated, activated, or both based on at least one of a location of an occupant within the vehicle or based on a viewing direction of the occupant.

Another example aspect of the disclosure is directed to one or more computer-readable media (e.g., non-transitory computer-readable media) that store instructions that are executable by a control circuit. The instructions, when executed, may cause the control circuit to perform operations. The operations may include receiving data indicating an inertial state of a vehicle, simulating a fluid based on the data indicating the inertial state of the vehicle, and outputting command instructions to cause the simulated fluid to be visualized within an interior of the vehicle using one or more lighting elements from among a plurality of activatable lighting elements of the vehicle.

Another example aspect of the disclosure is directed to a vehicle having the computing system described herein. For example, the vehicle may include a chassis and the computing system may include a control circuit configured to perform operations. The operations may include receiving data indicating an inertial state of the vehicle, simulating a fluid based on the data indicating the inertial state of the vehicle, and outputting command instructions to cause the simulated fluid to be visualized within an interior of the vehicle using one or more lighting elements from among a plurality of activatable lighting elements of the vehicle.

Other aspects of the disclosure are directed to various systems, apparatuses, non-transitory computer-readable media, user interfaces, and electronic devices.

These and other features, aspects, and advantages of various embodiments of the disclosure will become better understood with reference to the following description and appended claims. The accompanying drawings, which are incorporated in and constitute a part of this specification, illustrate example embodiments hereof and, together with the description, serve to explain the related principles.

BRIEF DESCRIPTION OF THE DRAWINGS

Detailed discussion of embodiments directed to one of ordinary skill in the art is set forth in the specification, which makes reference to the appended drawings, in which.

DETAILED DESCRIPTION

Overview

Figure 1:
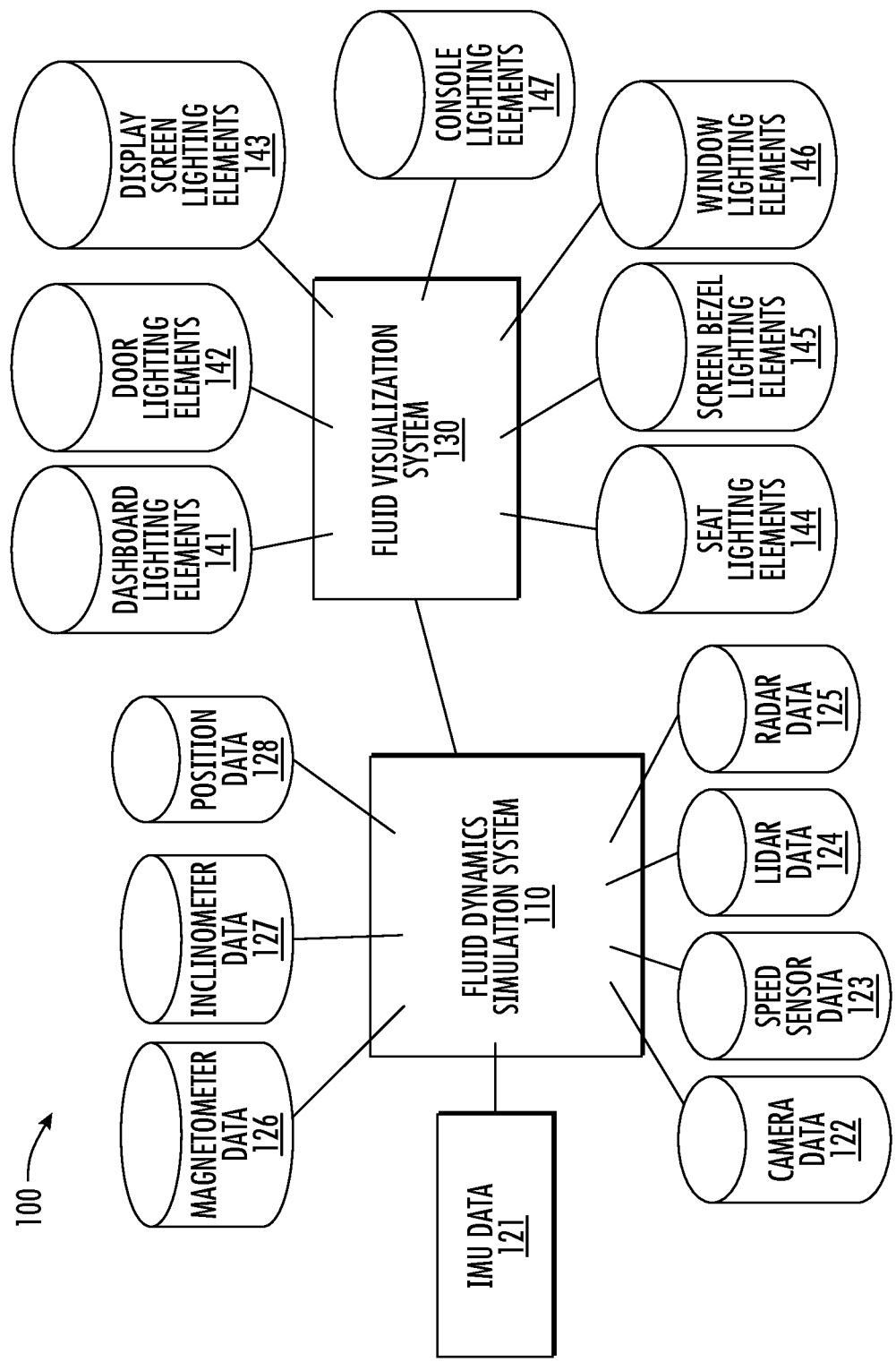
FIG. 1 illustrates a block diagram of an example motion sickness mitigation system according to example embodiments of the disclosure.

Aspects of the disclosure relate to methods and systems for mitigating motion sickness of an occupant in a vehicle. More particularly, the disclosure relates generally to methods and systems for simulating a fluid based on data indicating an inertial state of the vehicle and visualizing the simulated fluid within an interior of the vehicle using one or more lighting elements of the vehicle. Example embodiments of the disclosure are directed to simulating and visualizing fluid dynamics in vehicle interiors to improve passenger comfort during vehicle motion so as to prevent or mitigate motion sickness. For example, in some implementations the vehicle interior is augmented or modified with visual cues that are consistent with the motion sensed by the passengers' inner ears. That is, the visualization of the fluid dynamics closely emulates how humans measure accelerations and angular motion via the movement of fluid within their inner ears. Thus, fluid visualizations are much more adept at capturing the full range of inertial states felt by occupants in a vehicle.

For example, in some implementations a motion sickness mitigation system utilizes the vehicle's own inertial measurements as inputs to a physics-based model to simulate and visualize fluid dynamics, unlike artificial horizon simulations. The simulation result is visualized with lighting elements provided in the interior of the vehicle. Particular lighting elements may be utilized to ensure that visual cues are always present in the field-of-view of an occupant of the vehicle regardless of their in-vehicle activity.

The example methods and systems disclosed herein for mitigating motion sickness of an occupant in a vehicle do not require the occupant to wear virtual reality or augmented reality goggles. Furthermore, the example methods and systems disclosed herein do not require modifying how an occupant of a vehicle sees the outside environment (e.g., by modifying a window of the vehicle via augmented reality, dimming window sections, or adjusting the window transparency frequency). However, in some implementations the visualization of the simulated fluid may be visualized via a window (e.g., via projection integrated lighting elements).

The disclosure provides for utilizing sensors available on a vehicle (e.g., a consumer vehicle) to output data indicating an inertial state of the vehicle. For example, data may be received by a fluid dynamics simulation system from various sources including one or more inertial measurement units (IMU), one or more cameras, one or more speed sensors, one or more Light Detection and Ranging (LIDAR) sensors, one or more Radio Detection and Ranging (RADAR) sensors, one or more magnetometers, one or more inclinometers, one or more positioning sensors (e.g., global navigation satellite system (GLONASS) sensors, global positioning system (GPS) sensors, etc.), and the like.

The disclosure provides for the fluid dynamics simulation system using a physics-based fluid dynamics model to model a state of a fluid provided in a container or vessel based on the inertial state of the vehicle. Here, the container or vessel can include a shape which corresponds to a shape or configuration of one or more lighting elements which are disposed within the interior of the vehicle. That is, the fluid containers or vessels utilized by the fluid dynamics model can match a configuration of one or more lighting elements in the vehicle to be utilized for visualizing the simulated fluid. For example, when ambient lighting provided around a display screen (e.g., in a rectangular or U-shape) is selected or identified to be utilized for visualizing the simulated fluid, the fluid dynamics model may utilize a container having a similar shape (e.g., a rectangular or U-shaped container) to simulate the state of the fluid according to the inertial state of the vehicle. The fluid dynamics model can represent the configuration of the lighting elements as a network of nodes or as a mesh topology to simulate the motion of the fluid in the container, for example with respect to each node, based on the inertial state of the vehicle. When the model indicates that the fluid flows into a node the corresponding lighting element may be activated. When the model indicates that the fluid flows out of a node the corresponding lighting element may be deactivated. When the model indicates that a density value at a given node exceeds a first threshold value, an intensity of the corresponding lighting element may be increased. When the model indicates that a density value at a given node is less than a second threshold value, an intensity of the corresponding lighting element may be decreased. By way of example, a node (e.g., cell) in the model may have a finite volume which experiences changing densities based on how much fluid the node contains. For example, a node full with fluid may have a density value that matches the density of the fluid, while a node half-full with the fluid may have a density value that is halfway between the fluid and air. For example, the first threshold value may correspond to a node that is ¾ full and the second threshold value may correspond to a node that is ¼ full. However, other density values may be used and the disclosure is not limited to this example. In other implementations, the intensity of the lighting element may scale with the density of its corresponding node. In some implementations, as another example a density of the fluid itself may be reflected via the intensity of the fluid in the model. For example, when a density of the fluid at a given node exceeds a first threshold value, an intensity of the corresponding lighting element may be greater compared to an intensity of a corresponding lighting element for another fluid having a lower density.

In example embodiments, the fluid dynamics model may simulate a state of objects suspended in the fluid. For example, a fluid dynamics simulation system may implement the fluid dynamics model by modeling a state of a fluid as well as simulate granules (e.g. sand), air bubbles, filament structures, fiber-like structures (e.g. seaweed), or other objects which are suspended in the fluid. In some implementations, the fluid dynamics simulation system may implement the fluid dynamics model by modeling a state of granules (e.g. sand), air bubbles, filament structures, fiber-like structures (e.g. seaweed), or other objects, instead of modeling a state of a fluid.

In an embodiment, the simulated fluid as determined by the fluid dynamics simulation system may be visualized within an interior of the vehicle using one or more lighting elements from among a plurality of activatable lighting elements of the vehicle by a fluid visualization system. For example, the fluid visualization system may be configured to utilize (e.g., activate and/or deactivate) one or more lighting elements provided in the interior of the vehicle including dashboard lighting elements, door lighting elements, display screen lighting elements, seat lighting elements, screen bezel lighting elements, window lighting elements, console lighting elements, and the like. For example, a control circuit may control ambient lighting on the dashboard, lighting elements provided at infotainment display screen bezels, lighting provided at display screens embedded within various interior elements (e.g., on the dashboard, on interior door panels, etc.), on the display screen of infotainment display screen user interfaces, and the like.

In some implementations, the plurality of activatable lighting elements of the vehicle for mitigating motion sickness are limited or restricted to lighting elements which do not block or replace a view from inside the vehicle to the outside of the vehicle. In some implementations, the plurality of activatable lighting elements of the vehicle for mitigating motion sickness are provided or selected such that visual cues about the inertial state of the vehicle are visible from every field-of-view within the interior of the vehicle, for example, regardless of an activity engaged in by an occupant of the vehicle.

The motion mitigation system may be implemented as part of an active comfort system that enables a user to select various settings. For example, various user interfaces may be implemented to allow a user to select locations within the vehicle to which the motion mitigation system is to be applied. For example, various user interfaces may be implemented to allow a user to select lighting colors, objects that are to be simulated as being suspended in the fluid, and a viscosity of the fluid.

Example aspects of the disclosure provide a number of technical effects and benefits. As one example, the disclosure facilitates improvements to automotive technology by enabling a computing system, such as a system onboard a vehicle, to prevent or reduce motion sickness experienced by occupants of a vehicle. This can improve vehicle control and reduce user input with comfort features of the vehicle (e.g., temperature, window, etc.) that an occupant may otherwise seek in an effort to mitigate motion sickness. Reduced interaction with such features can reduce the use of the vehicle's limited computing resources that would need to be used to process the user input.

Mitigating motion sickness experienced by occupants of a vehicle may improve a travelling experience of the occupant. As another example, limiting the use of lighting elements to particular zones or locations for mitigating motion sickness by identifying the location of occupants in the vehicle (rather than utilizing all activatable lighting elements) achieves resource savings (e.g., power savings, CPU usage, etc.).

In some implementations, a division of computing tasks between an onboard system and a remote system may be provided. For example, simulating a fluid (via a fluid dynamics model) based on the data indicating the inertial state of the vehicle may be performed by a remote server computing system in some implementations. Because some of the computing tasks may be performed remote from the vehicle at generally stronger computing systems, onboard processing requirements may be reduced. Therefore, mitigating motion sickness may be implemented on vehicles lacking hardware components for modeling a fluid based on an inertial state of a vehicle. This may beneficially provide for a reduced computing resource requirement for mitigating motion sickness and a reduced cost associated with vehicles capable of mitigating motion sickness.

Example Systems

With reference now to the drawings, example embodiments will be discussed in further detail.

FIG. 1 illustrates a block diagram of an example motion sickness mitigation system 100 according to example embodiments hereof. The motion sickness mitigation system 100 may be implemented by a computing system, for example, a vehicle computing system. In some implementations, aspects of the disclosure may be performed by a server computing system (e.g., a remote server system including a cloud server system). For example, a server computing system may be implemented to simulate a fluid based on data indicating an inertial state of a vehicle and provide the simulated fluid to the vehicle computing system. In addition, or alternatively, a server computing system may be implemented to output command instructions to the vehicle computing system to cause the simulated fluid to be visualized within an interior of the vehicle using one or more lighting elements from among a plurality of activatable lighting elements of the vehicle.

The motion sickness mitigation system 100 may include a fluid dynamics simulation system 110 and a fluid visualization system 130.

The fluid dynamics simulation system 110 may be configured to utilize various inputs to model or simulate movement (or lack of movement) of a fluid according to an inertial state of a vehicle. For example, data may be received from various sources including one or more inertial measurement units (IMU), one or more cameras, one or more speed sensors, one or more Light Detection and Ranging (LIDAR) sensors, one or more Radio Detection and Ranging (RADAR) sensors, one or more magnetometers, one or more inclinometers, one or more positioning sensors (e.g., global navigation satellite system (GLONASS) sensors, global positioning system (GPS) sensors, etc.), and the like. As illustrated in FIG. 1, the fluid dynamics simulation system 110 may receive one or more inputs including IMU data 121, camera data 122, speed sensor data 123, LIDAR data 124, RADAR data 125, magnetometer data 126, inclinometer data 127, position data 128, and the like.

The fluid dynamics simulation system 110 may be configured to utilize information or data relating to the attitude (e.g., roll, pitch, and/or yaw angles) of the vehicle, and inertial measurements (e.g., linear accelerations, angular velocities, etc.) as inputs. For example, the inputs may be communicated to the fluid dynamics simulation system 110 via a vehicle bus. In some implementations, the inputs may be communicated to a server system via a wireless network. For example, in some implementations the IMU may be a primary or only source of input data to the fluid dynamics simulation system 110 and data from other sources (e.g., wheel speed sensors, camera images, LIDAR measurements, RADAR measurements, magnetometer measurements, inclinometer measurements, position measurements, etc.) may augment the data provided by the IMU. For example, the IMU may provide data relating to the linear accelerations and angular velocity of the vehicle along six degrees of freedoms. In some implementations, data relating to an inertial state of the vehicle may be provided from a source other than a source provided at the vehicle, for example, via inertial sensors (e.g., accelerometers and/or gyroscopes) included in a computing device disposed in the vehicle (e.g., a smartphone having an inertial measurement unit and/or other sensors). The computing device may be disposed in a stationary or fixed manner to accurately reflect the inertial state of the vehicle.

The fluid dynamics simulation system 110 may be configured to utilize a physics-based fluid dynamics model to simulate a fluid according to an inertial state of the vehicle. In some implementations, the fluid dynamics simulation system 110 may be configured to utilize a physics-based fluid dynamics model to simulate the fluid according to the inertial state of the vehicle and according to a known or preset vessel or container having a shape that corresponds to an arrangement or configuration of lighting elements that are provided in the vehicle. That is, the simulated fluid containers or vessels modeled by the fluid dynamics simulation system 110 are configured to match a configuration of lighting elements in the vehicle to be utilized for visualizing the simulated fluid. For example, when ambient lighting provided around a display screen (e.g., in a rectangular or U-shape) is selected or identified to be utilized for visualizing the simulated fluid, the fluid dynamics model may utilize a container having a similar shape (e.g., a rectangular or U-shaped container) to simulate the state of the fluid according to the inertial state of the vehicle.

For example, the fluid dynamics simulation system 110 may implement the fluid dynamics model by simulating the state of the fluid by modeling the container as a configuration of nodes which correspond to a configuration of lighting elements, as described later with respect to the examples of FIGS. 4A-4C.

In some implementations, the fluid dynamics simulation system 110 may implement the fluid dynamics model by modeling a state of a fluid as well as simulate granules (e.g. sand), air bubbles, filament structures, fiber-like structures (e.g. seaweed), or other objects which are suspended in the fluid. In some implementations, the fluid dynamics simulation system 110 may implement the fluid dynamics model by modeling a state of granules (e.g. sand), air bubbles, filament structures, fiber-like structures (e.g. seaweed), or other objects, instead of modeling a state of a fluid.

In some implementations, the fluid dynamics simulation system 110 may be configured to adjust a viscosity of the fluid when implementing the fluid dynamics model to modify the sensitivity of the fluid to the motion of the vehicle. For example, the fluid dynamics simulation system 110 may be configured to increase a viscosity of the fluid when implementing the fluid dynamics model in response to the motion of the vehicle being greater than a threshold value. For example, the fluid dynamics simulation system 110 may utilize a viscosity value similar to that of the viscosity of water (e.g., 1.00 centipoise (cP)) as a default value. However, other viscosity values may be utilized (e.g., 0.6 cP, 1.5 cP, 2.0 cP, 50 cP, 5,000 cP, etc.). In some implementations, a user may be enabled to change the viscosity value, for example, via a user interface, according to a user preference.

The fluid visualization system 130 may be configured to visualize the simulated fluid as determined by the fluid dynamics simulation system 110 within an interior of the vehicle using one or more lighting elements from among a plurality of activatable lighting elements of the vehicle. For example, the fluid visualization system 130 may be configured to utilize (e.g., activate and/or deactivate) one or more lighting elements provided in the interior of the vehicle including dashboard lighting elements 141, door lighting elements 142, display screen lighting elements 143, seat lighting elements 144, screen bezel lighting elements 145, window lighting elements 146, console lighting elements 147, and the like. For example, a control circuit may control ambient lighting on the dashboard, lighting elements provided at infotainment display screen bezels, lighting provided at display screens embedded within various interior elements (e.g., on the dashboard, on interior door panels, etc.), on the display screen of infotainment display screen user interfaces, and the like.

In some implementations, the plurality of activatable lighting elements of the vehicle for mitigating motion sickness are limited or restricted to lighting elements which do not block or replace a view from inside the vehicle to the outside of the vehicle. In some implementations, the plurality of activatable lighting elements of the vehicle for mitigating motion sickness are provided or selected such that visual cues about the inertial state of the vehicle are visible from every field-of-view within the interior of the vehicle, for example, regardless of an activity engaged in by an occupant of the vehicle.

In some implementations, the plurality of activatable lighting elements of the vehicle for mitigating motion sickness are provided or selected such that visual cues about the inertial state of the vehicle are visible from specified zones of the vehicle. For example, a particular zone for which the motion sickness mitigation system 100 is to be applied to may be specified according to a user input (e.g., via a user interface including through a voice input, touch input, etc.). For example, a particular zone for which the motion sickness mitigation system 100 is to be applied to may be specified according to the vehicle detecting a location of occupants in the vehicle (e.g., via seat detection systems including via weight sensors, camera detection, and the like).

In some implementations, the plurality of activatable lighting elements of the vehicle for mitigating motion sickness are provided or selected such that visual cues about the inertial state of the vehicle are visible according to a location of an occupant within the vehicle. For example, lighting elements which are to be controlled for implementing the motion sickness mitigation system 100 may be specified according to an occupant location. For example, the occupant location (e.g., driver seat, front passenger seat, rear passenger seats, etc.) can be specified according to a user input (e.g., via a user interface including through a voice input, touch input, etc.). For example, the occupant location may be specified according to the vehicle detecting a location of occupants in the vehicle (e.g., via seat detection systems including via weight sensors, camera detection, and the like).

In some implementations, the plurality of activatable lighting elements of the vehicle for mitigating motion sickness are provided or selected such that visual cues about the inertial state of the vehicle are visible according to a direction in which a vehicle occupant is looking. For example, lighting elements which are to be controlled for implementing the motion sickness mitigation system 100 may be specified according to a direction in which an occupant is looking (e.g., for a predetermined duration of time or longer). For example, the direction in which the vehicle occupant is looking may be determined according to the vehicle detecting a viewing direction of the occupant (e.g., via camera detection, gaze detection, eye trackers, and the like). As an example, if an occupant faces in a rearward direction of the vehicle then lighting elements which are in a line of sight or field of view of the occupant may be controlled by the motion sickness mitigation system 100 instead of lighting elements which are behind the occupant or outside the field of view of the occupant. To avoid frequent changes to lighting elements which are to be utilized by the motion sickness mitigation system 100 due to an occupant changing their viewing direction frequently, the motion sickness mitigation system 100 may ensure that the occupant maintains a viewing direction for a minimum duration of time (e.g., a predetermined duration of time or longer) before determining whether to change or update lighting elements which are to be controlled for implementing the motion sickness mitigation system 100 according to the viewing direction of the occupant.

The fluid visualization system 130 may be configured to visualize the simulated fluid as determined by the fluid dynamics simulation system 110 within the interior of the vehicle using one or more lighting elements from among the plurality of activatable lighting elements of the vehicle according to various methods. For example, a lighting intensity may be varied according to a density of a node determined based on the simulated fluid. For example, a color of the lighting elements may be changed according to the simulated fluid. Example visualizations are discussed below with respect to FIGS. 2A-2C.

Figure 2A:
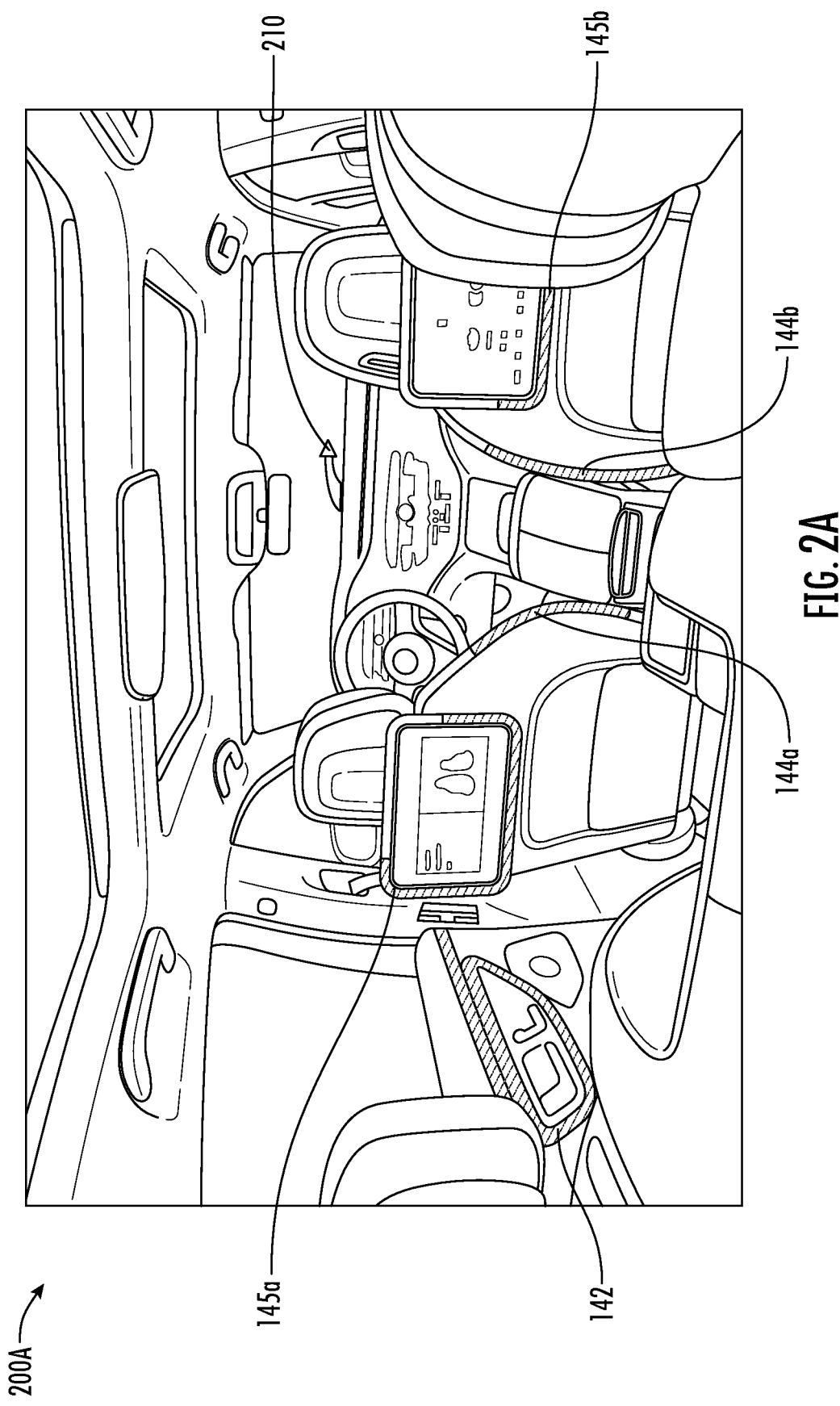
FIGS. 2A-2C illustrate example implementations of the motion sickness mitigation system, according to example embodiments of the disclosure.

Referring to FIG. 2A, an example implementation of the motion sickness mitigation system is shown, according to example embodiments of the disclosure. For example, FIG. 2A illustrates via arrow 210 that the vehicle 200A is turning right. In the example of FIG. 2A the arrow 210 is an image annotation and is not actually displayed on the windshield of the vehicle 200A. Sensors including the inertial measurement unit may provide data indicating the inertial state of the vehicle 200A to the fluid dynamics simulation system 110 which may model a simulated fluid according to lighting elements which are to be activated. For example, the fluid dynamics simulation system 110 may treat each respective interior component having lighting elements as a separate container when modeling the fluid, or the fluid dynamics simulation system 110 may combine interior components having lighting elements and treat the combined interior components as a single container when modeling the fluid.

As illustrated in the example of FIG. 2A, lighting elements which are activatable for implementing aspects of the motion sickness mitigation system 100 (e.g., for visualizing the simulated fluid) include door lighting elements 142, seat lighting elements 144a and seat lighting elements 144b, and screen bezel lighting elements 145a and screen bezel lighting elements 145b. For example, the lighting elements may be activated using a particular color (e.g., blue ambient lighting). For example, when the vehicle 200A is turning right, the fluid may be simulated via the fluid dynamics model as experiencing a centrifugal force that pulls the fluid to the left. The simulated fluid may be visualized within the interior of the vehicle 200A via the door lighting elements 142, seat lighting elements 144a and seat lighting elements 144b, and screen bezel lighting elements 145a and screen bezel lighting elements 145b such that the lighting elements act as a visual cue which is consistent with what the occupants in the vehicle 200A feel, mitigating their susceptibility to motion sickness.

Figure 2B:
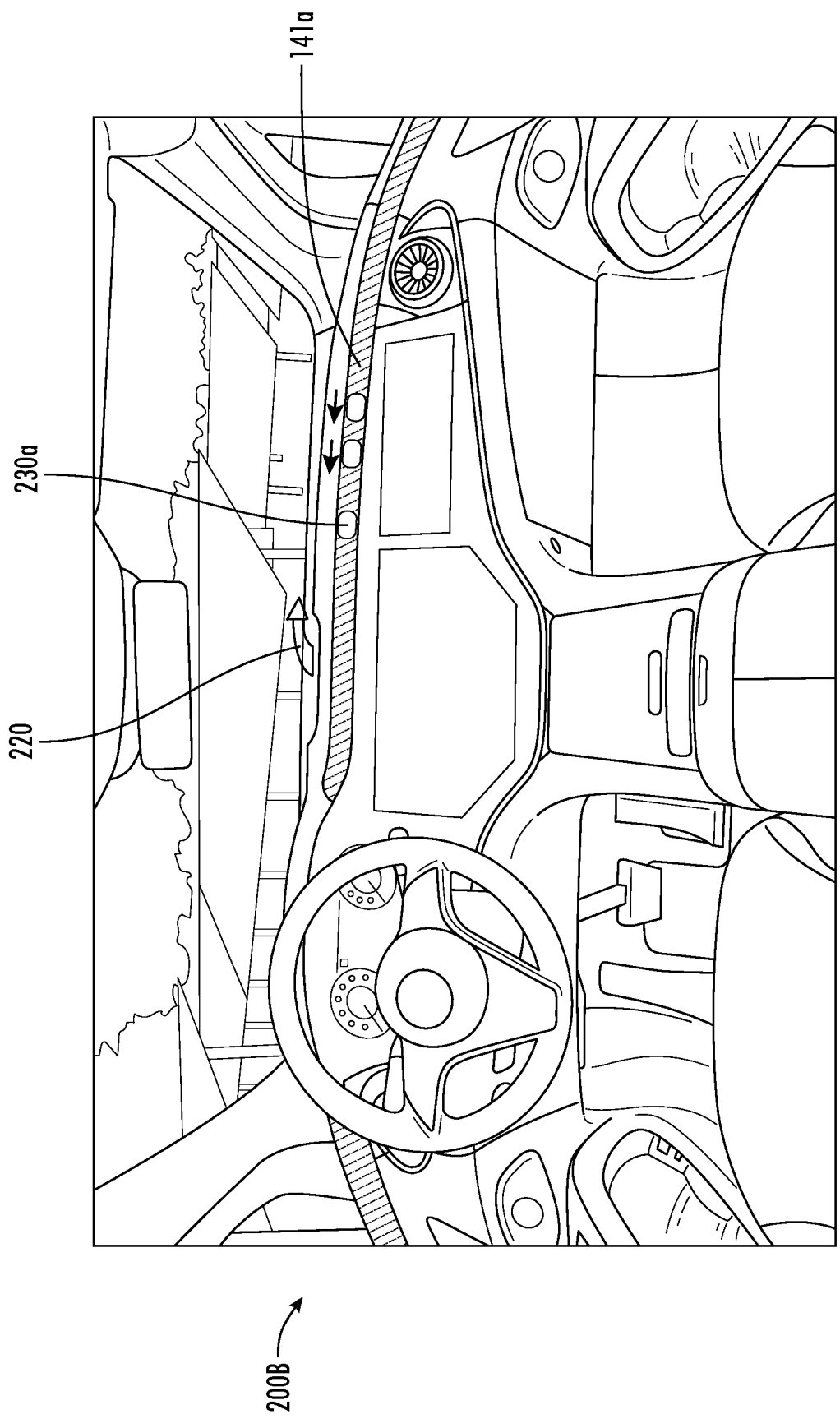
Figure 2C:
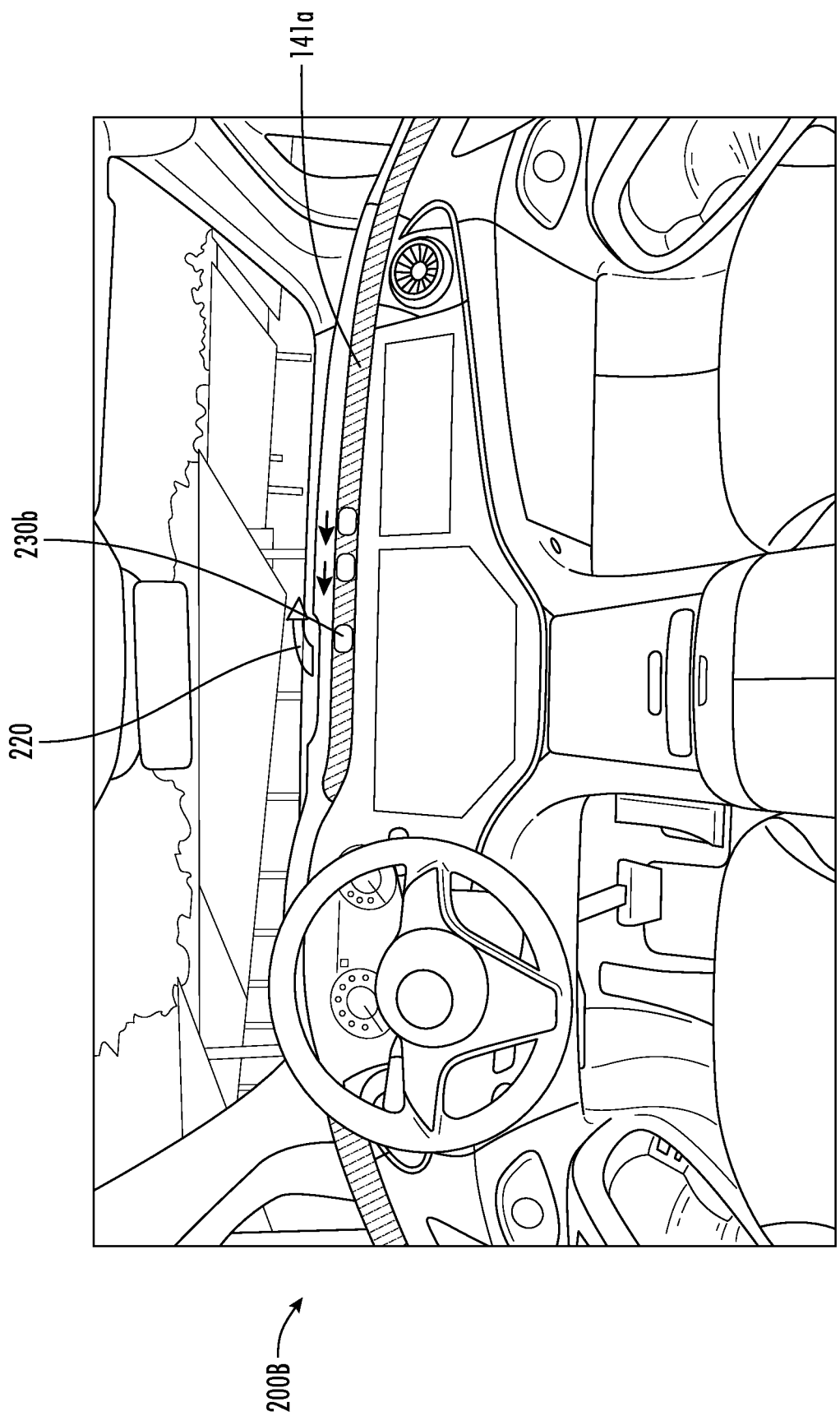

Referring to FIGS. 2B-2C, another example implementation of the motion sickness mitigation system is shown, according to example embodiments of the disclosure. For example. FIG. 2B illustrates via arrow 220 that the vehicle 200B is turning right. In the example of FIG. 2B the arrow 220 is an image annotation and is not actually displayed on the windshield of the vehicle 200B. Sensors including the inertial measurement unit may provide data indicating the inertial state of the vehicle 200B to the fluid dynamics simulation system 110 which may model a simulated fluid according to lighting elements which are to be activated. For example, the fluid dynamics simulation system 110 may treat each respective interior component having lighting elements as a separate container when modeling the fluid, or the fluid dynamics simulation system 110 may combine interior components having lighting elements and treat the combined interior components as a single container when modeling the fluid.

The fluid dynamics simulation system 110 may model the simulated fluid itself and one or more simulated objects in the fluid. For example, the one or more objects may include one or more of: (i) granules, (ii) air bubbles, (iii) filaments, or (iv) fiber-like structures. In some implementations, the fluid dynamics simulation system 110 may model the simulated one or more objects in the fluid instead of the fluid.

In the example of FIGS. 2B-2C, the vehicle 200B has fluids simulated and visualized using dashboard lighting elements 141a provided on (or integrated with) the dashboard (e.g., using blue ambient lighting). In addition, in the example of FIG. 2B, the fluid is simulated with suspended air bubbles 230a (as indicated by the lack of light). When the vehicle is turning right, the inertia of the air bubbles 230a makes the air bubbles appear as if they are moving from left to right from an occupants' point of view. For example, as shown in FIG. 2C air bubbles 230b are disposed further to the left on the dashboard compared to the air bubbles 230a in FIG. 2B. The simulated fluid together with the simulated air bubbles may be visualized within the interior of the vehicle 200A via dashboard lighting elements 141a such that activation and deactivation of certain lighting elements from the dashboard lighting elements 141a act as a visual cue which is consistent with what the occupants in the vehicle 200A feel, mitigating their susceptibility to motion sickness.

Figure 3:
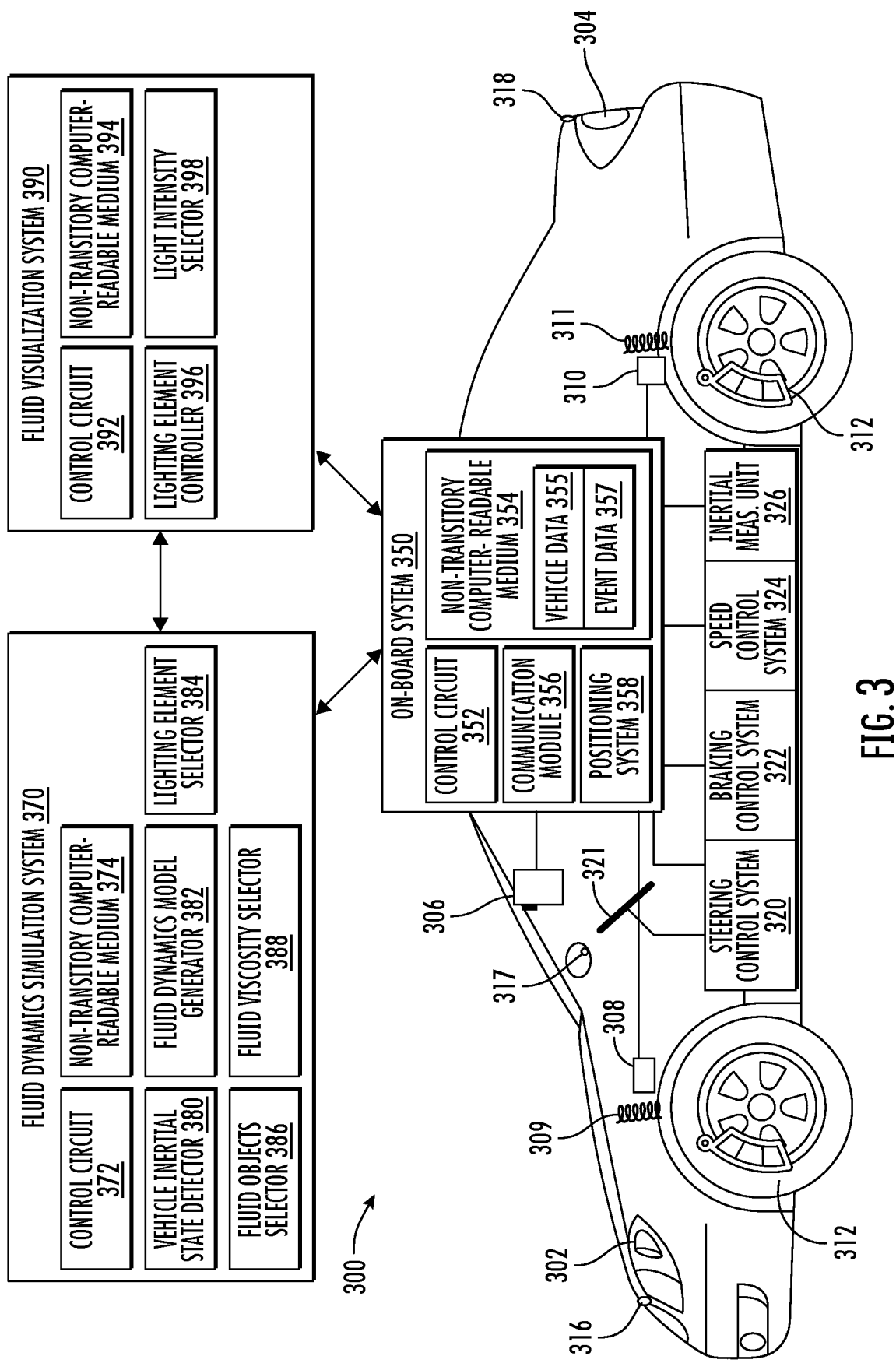
FIG. 3 illustrates a block diagram of an example vehicle and motion sickness mitigation system, according to example embodiments of the disclosure.

FIG. 3 illustrates a block diagram of an example vehicle 300 and motion sickness mitigation system including the fluid dynamics simulation system 370 and fluid visualization system 390, according to example embodiments hereof. The motion sickness mitigation system and the vehicle 300 of FIG. 3 may represent the same systems as the motion sickness mitigation systems and vehicles depicted in other drawings (e.g., FIGS. 1 and 2A-2C). In some implementations, the fluid dynamics simulation system 370 and fluid visualization system can be included in the onboard system 350.

The vehicle 300 may be a vehicle configured to mitigate motion sickness of one or more occupants of the vehicle, according to example aspects of the disclosure. The vehicle 300 may be a vehicle that is operable by a user. In an embodiment, the vehicle 300 may be an automobile or another type of ground-based vehicle that is manually driven by a user. For example, the vehicle 300 may be a Mercedes-Benz® car or van. The vehicle 300 may include operator-assistance functionality such as cruise control, advanced driver assistance systems, etc. In some implementations, the vehicle 300 may be a fully or semi-autonomous vehicle.

The vehicle 300 may include a power train and one or more power sources. The power train may include a motor, e-motor, transmission, driveshaft, axles, differential, e-components, gear, etc. The power sources may include one or more types of power sources. For example, the vehicle 300 may be a fully electric vehicle (EV) that is capable of operating a powertrain of the vehicle 300 (e.g., for propulsion) and the vehicle's onboard functions using electric batteries. In an embodiment, the vehicle 300 may use combustible fuel. In an embodiment, the vehicle 300 may include hybrid power sources including, for example, a combination of combustible fuel and electricity. In an aspect, the vehicle 300 may be a commercially available consumer vehicle.

Known components of vehicle 300 (e.g., an engine, passenger seats, windows, tires and wheels) are not illustrated and/or discussed herein in detail for the purpose of brevity. One of ordinary skill in the art will understand the operation of known vehicle components in vehicle 300.

The vehicle 300 may include a front location and/or a rear location. The vehicle may include one or more driving lights, such as headlights 302 and/or rear lights 304. The vehicle 300 may include a front suspension 309 and/or a rear suspension 311. The front suspension 309 may be fitted with a vibration sensor 308. The vibration sensor 308 may record vibration data descriptive of vibrations, impacts, and/or other forces acting on the front suspension 309. Similarly, the rear suspension 311 may be fitted with a vibration sensor 310 that records vibration data at the rear suspension 311. It should be understood that the vibration sensors 308, 310 may be associated with an individual wheel, with an axle, and/or with any other suitable component of the vehicle 300. In addition to facilitating control of the vehicle 300, the detections from the vibration sensors 308 can be used as input data to the fluid dynamics simulation system 370 to be used for determining an inertial state of the vehicle 300.

The vehicle 300 may include a front brake 312 and/or a rear brake 314. The brakes 312, 314 may be operable to reduce a rotational speed of the wheels of the vehicle 300. The brakes 312, 314 may be controlled by a braking control system 322 of the vehicle 300. In an embodiment, the braking control system 322 may identify heavy braking events, loss of traction while braking, and/or other abnormal braking events and engage an anti-lock braking system (not illustrated) and/or other suitable remedial systems. In addition to facilitating control of the vehicle 300, the detections from the braking control system 322 may indicate a deceleration condition that can be measured by the inertial measurement unit 326 (e.g., via one or more accelerometers and/or gyroscopes) and an output of the inertial measurement unit 326 can be used as input data to the fluid dynamics simulation system 370 to be used for determining an inertial state of the vehicle 300.

The vehicle 300 may include various systems for controlling the vehicle 300 and/or obtaining inertial (e.g., motion) data relating to the vehicle 300. The vehicle 300 may include a steering control system 320. A driver may interact with a steering wheel 321 to control the heading of the vehicle 300. In response to the driver's interaction with the steering wheel 321, the steering control system 320 may adjust a direction of one or more components of the vehicle 300 to steer the vehicle 300. Additionally and/or alternatively, the vehicle 300 may include a speed control system 324 that controls a speed of the vehicle 300. For instance, a driver may interact with a throttle, gas pedal, and/or other interface to cause the vehicle 300 to accelerate and/or decelerate. Additionally and/or alternatively, the vehicle 300 may include a cruise control system or other automated system to maintain, adjust, or otherwise affect the speed of the vehicle 300. The speed control system 324 may report a current speed of the vehicle 300. In addition to facilitating control of the vehicle 300, the detections from the speed control system 324 may be used as input data (e.g., speed sensor data 123) to the fluid dynamics simulation system 370 to be used for determining an inertial state of the vehicle 300.

Furthermore, the vehicle 300 may include the inertial measurement unit 326 that reports acceleration information (e.g., linear accelerations) and velocity information (e.g., angular velocities) of the vehicle 300. In addition to facilitating control of the vehicle 300, the detections from the inertial measurement unit 326 may be used as input data (e.g., IMU data 121) to the fluid dynamics simulation system 370 to be used for determining an inertial state of the vehicle 300.

The vehicle 300 may include one or more cameras disposed on and/or within the vehicle 300. For instance, the vehicle 300 may include one or more dash cameras 306, one or more hood cams 316, one or more mirror cams 317, one or more rear cams 318, and/or any other suitable cameras. The camera(s) 306, 316, 317, 318 may capture image data and/or video data depicting an internal and/or external environment of the vehicle 300 during operation. The camera(s) 306, 316, 317, 318 may capture video data in any suitable format. As one example, the camera(s) 306, 316, 317, 318 may capture video data as a stream of images in any suitable image format, such as JPEG, BMP, PNG, etc. and/or any suitable proprietary formats. As another example, the camera(s) 306, 316, 317, 318 may capture video data in any suitable video format, such as MP4, AVI, AVCHD, DV, etc. and/or any suitable proprietary formats. In addition to facilitating control of the vehicle 300, the detections from the camera(s) 306, 316, 317, 318 may indicate a location or zone of occupants in the vehicle 300 for determining one or more areas in which the motion sickness mitigation system may be applied. In addition, or alternatively, the detections from the camera(s) 306, 316, 317, 318 may be used to determine whether certain lighting elements should be utilized by the motion sickness mitigation system based on a location or zone of the occupants of the vehicle detected by the camera(s) 306, 316, 317, 318. In addition, or alternatively, the detections from the camera(s) 306, 316, 317, 318 may be used as input data (e.g., camera data 122) to the fluid dynamics simulation system 370 to be used for determining an inertial state of the vehicle 300.

The vehicle 300 may include other sensors or devices for controlling the vehicle 300 which are not specifically shown in FIG. 3 (e.g., a magnetometer, an inclinometer, a LIDAR, a RADAR, and the like). In addition to facilitating control of the vehicle 300, the detections from these other sensors or devices may be used as input data (e.g., LIDAR data 124, RADAR data 125, magnetometer data 126, inclinometer data 127, and the like) to the fluid dynamics simulation system 370 to be used for determining an inertial state of the vehicle 300.

The vehicle 300 may include an on-board system 350. The on-board system 350 may be configured to perform some or all operations for motion sickness mitigation as described herein. The on-board system 350 may include a control circuit 352. In an embodiment, the control circuit 352 may include one or more processors (e.g., microprocessors), one or more processing cores, a programmable logic circuit (PLC) or a programmable logic/gate array (PLA/PGA), a field programmable gate array (FPGA), an application specific integrated circuit (ASIC), or any other control circuit. In some implementations, the control circuit 352 and/or on-board system 350 may be part of, or may form, a vehicle control unit (also referred to as a vehicle controller) that is embedded or otherwise disposed in the vehicle 300 (e.g., a Mercedes-Benz® car or van). For example, the vehicle controller may be or may include an infotainment system controller (e.g., an infotainment head-unit), a telematics control unit (TCU), an electronic control unit (ECU), a central powertrain controller (CPC), a central driving and charging controller (CDCC), centralized in-vehicle integration computer (CIVIC), a central exterior & interior controller (CEIC), a zone controller, or any other controller (the term "or" and "and/or" may be used interchangeably herein).

In an embodiment, the on-board system 350 may include a non-transitory computer-readable medium 354 (also referred to as memory 354). The non-transitory computer-readable medium 354 may be a memory device, also referred to as a data storage device, which may include an electronic storage device, a magnetic storage device, an optical storage device, an electromagnetic storage device, a semiconductor storage device, or any suitable combination thereof. The non-transitory computer-readable medium may form, e.g., a hard disk drive (HDD), a solid state drive (SDD) or solid state integrated memory, a random access memory (RAM), a read-only memory (ROM), an erasable programmable read-only memory (EPROM or Flash memory), a static random access memory (SRAM), dynamic random access memory (DRAM), a portable compact disc read-only memory (CD-ROM), a digital versatile disk (DVD), and/or a memory stick. In some cases, the non-transitory computer-readable medium 354 may store computer-executable instructions or computer-readable instructions, such as instructions to perform any of the methods 600, 610, 630, 640 of FIGS. 6A-6D.

In various embodiments, the terms "computer-readable instructions" and "computer-executable instructions" are used to describe software instructions or computer code configured to carry out various tasks and operations. In various embodiments, if the computer-readable or computer-executable instructions form modules, the term "module" refers broadly to a collection of software instructions or code configured to cause the control circuit 352 to perform one or more functional tasks. The modules and computer-readable/executable instructions may be described as performing various operations or tasks when a control circuit or other hardware component is executing the modules or computer-readable instructions.

In an embodiment, the non-transitory computer-readable medium 354 may store vehicle data 355 that describes aspects of the vehicle, such as make, model, year, serial number, software/firmware versions, and/or other vehicle aspects. In an embodiment, the non-transitory computer-readable medium 354 may store event data 357. The event data 357 may describe interactions with features, such as reportable events. For instance, the event data 357 may include information such as which component of the vehicle 300 interacted with the feature, sensor data from sensor(s) associated with that component, timestamps associated with the event data, positioning data associated with the event, and/or other suitable data for recording and/or reporting interactions with features of a travelway.

The on-board system may include or may be in communication with a positioning system 358. The positioning system 358 may be any suitable positioning system and/or combinations thereof. As one example, the positioning system 358 may be or may include a satellite positioning system, such as GPS or GLONASS. As another example, the positioning system 358 may segment a travelway into a plurality of travelway segments. The positioning system 358 may output positioning data describing which travelway segment(s) the vehicle 300 is located or positioned within. For instance, the positioning system 358 may compare coordinates (e.g., satellite coordinates) of the vehicle 300 to coordinates associated with travelway segments to identify which segments the vehicle 300 is positioned within. Additionally and/or alternatively, the positioning system 358 may utilize computer vision techniques, such as lane recognition techniques, to identify which lane and/or segment of a travelway the vehicle 300 is positioned within. In addition to facilitating control and/or navigation of the vehicle 300, the detections from the positioning system 358 may be used as input data (e.g., position data 128) to the fluid dynamics simulation system 370 to be used for determining an inertial state of the vehicle 300.

The on-board system 350 may communicate with a fluid dynamics simulation system 370 that may be integrated with the vehicle 300 or may be provided remotely from the vehicle 300. For example, the fluid dynamics simulation system 370 may be or may include a remote server. The fluid dynamics simulation system 370 may include one or more control circuits 372. In an embodiment, the one or more control circuits 372 may include one or more processors (e.g., microprocessors), one or more processing cores, a programmable logic circuit (PLC) or a programmable logic/gate array (PLA/PGA), a field programmable gate array (FPGA), an application specific integrated circuit (ASIC), or any other control circuit. In some implementations, the one or more control circuits 372 may be embodied as the one or more control circuits 352. That is, the one or more control circuits 352 of the on-board system 350 may perform the operations of the one or more control circuits 372.

In an embodiment, the fluid dynamics simulation system 370 may include a non-transitory computer-readable medium 374 (also referred to as memory 374). The non-transitory computer-readable medium 374 may be a memory device, also referred to as a data storage device, which may include an electronic storage device, a magnetic storage device, an optical storage device, an electromagnetic storage device, a semiconductor storage device, or any suitable combination thereof. The non-transitory computer-readable medium may form, e.g., a hard disk drive (HDD), a solid state drive (SDD) or solid state integrated memory, a random access memory (RAM), a read-only memory (ROM), an erasable programmable read-only memory (EPROM or Flash memory), a static random access memory (SRAM), dynamic random access memory (DRAM), a portable compact disc read-only memory (CD-ROM), a digital versatile disk (DVD), and/or a memory stick. In some implementations, the non-transitory computer-readable medium 374 may be embodied as the non-transitory computer-readable medium 354. That is, non-transitory computer-readable medium 354 of the on-board system 350 may perform the operations of the non-transitory computer-readable medium 374.

The fluid dynamics simulation system 370 may implement or otherwise provide services that facilitate motion sickness mitigation according to aspects of the disclosure. The fluid dynamics simulation system 370 may be in communication with various vehicle systems or sensors, for example via on-board system 350, and input data received from the various vehicle systems or sensors can be used by the fluid dynamics simulation system 370 for determining an inertial state of the vehicle 300. The fluid dynamics simulation system 370 may store the input data in non-transitory computer-readable medium 374 for use in determining an inertial state of the vehicle 300. In addition to input data received from vehicle 300, the fluid dynamics simulation system 370 may obtain data through communication with remote or third-party systems. For example, the fluid dynamics simulation system 370 may obtain input data relating to an inertial state of the vehicle 300 from an external device (e.g., a smartphone).

The fluid dynamics simulation system 370 may include a vehicle inertial state detector 380 which is configured to receive input data (e.g., one or more of IMU data 121, camera data 122, speed sensor data 123, LIDAR data 124, RADAR data 125, magnetometer data 126, inclinometer data 127, position data 128, and the like) and is configured to determine an inertial state of the vehicle 300 based on the received input data. For example, the input data may indicate that the vehicle 300 is making a turn, stopping (decelerating), accelerating, climbing or parked at an upward angle, descending or parked at a downward angle, at a stop, level, and the like.

The fluid dynamics simulation system 370 may include a fluid dynamics model generator 382 which is configured to simulate a fluid based on the input data indicating the inertial state of the vehicle 300. The fluid dynamics model generator 382 may be configured to utilize a physics-based fluid dynamics model to simulate a fluid according to the inertial state of the vehicle 300. In some implementations, the fluid dynamics model generator 382 may be configured to utilize a physics-based fluid dynamics model to simulate the fluid according to the inertial state of the vehicle 300 and according to a known or preset vessel or container having a shape that corresponds to an arrangement or configuration of one or more lighting elements that are provided in the vehicle. That is, the simulated fluid containers or vessels modeled by the fluid dynamics model generator 382 are configured to match the lighting elements in the vehicle to be utilized for visualizing the simulated fluid. For example, non-transitory computer-readable medium 374 and/or non-transitory computer-readable medium 354 may store in a database or look-up table a mapping between a lighting element configuration and a specified container or vessel. For example, a linear arrangement of lighting elements (e.g., along a seat, door, dashboard, etc.) may correspond to a first container used by the fluid dynamics model that is linear and in the form of a tube. For example, a box-shaped arrangement of lighting elements (e.g., lighting elements provided on a bezel disposed around a display screen, a configuration of lighting elements that surround an interior door handle, etc.) may correspond to a second container used by the fluid dynamics model that is also box-shaped and in the form of a tube. For example, in some implementations some simulated fluid containers or vessels modeled by the fluid dynamics model generator 382 may correspond respectively to individual configurations of lighting elements disposed in the interior of the vehicle. For example, in some implementations some simulated fluid containers or vessels modeled by the fluid dynamics model generator 382 may correspond to a combination of configurations of lighting elements disposed in the interior of the vehicle. For example, in FIG. 2A, a simulated fluid container or vessel modeled by the fluid dynamics model generator 382 may correspond to the combination of seat lighting elements 144a and seat lighting elements 144b. For example, in some implementations some simulated fluid containers or vessels modeled by the fluid dynamics model generator 382 may include portions which are not visible or which do not correspond to a particular lighting element configuration (e.g., portions which are not used for visually representing the simulated fluid). For example, in FIG. 2B, a simulated fluid container or vessel modeled by the fluid dynamics model generator 382 may include a ring that extends around the vehicle where a portion of the ring corresponds to dashboard lighting elements 141a and other portions of the ring do not correspond to the dashboard lighting elements 141a. That is, the simulated ring extends around the vehicle and partly encompasses the portion corresponding to dashboard lighting elements 141a where only the part of the ring that coincides with the dashboard lighting elements 141a is visualized with lighting elements for representing the simulated fluid.

For example, lighting elements which are to be utilized for visualizing the simulated fluid may be determined by the lighting element selector 384. In some implementations, the lighting element selector 384 may be configured to select all lighting elements in the vehicle 300 as being activatable for purposes of implementing the motion sickness mitigation system. In some implementations, the lighting element selector 384 may be configured to select those lighting elements in the vehicle 300 which are disposed in a particular zone or seat in which occupants are located (e.g., as determined by the vehicle 300 and/or as determined based on an input received from a user) as being activatable for purposes of implementing the motion sickness mitigation system. In some implementations, the lighting element selector 384 may be configured to select those lighting elements in the vehicle 300 which are disposed in a field of view of the occupants (e.g., as determined by the vehicle 300 and/or as determined based on an input received from a user) as being activatable for purposes of implementing the motion sickness mitigation system. For example, if the lighting element selector 384 determines no occupants are located in a rear zone or a rear seat, then lighting element selector 384 may be configured to exclude lighting elements visible from the rear zone or the rear seat as possible activatable lighting elements for implementation with the motion sickness mitigation system. For example, if the lighting element selector 384 determines occupants are located in a front zone or a front seat, then lighting element selector 384 may be configured to include lighting elements visible from the front zone or the front seat as possible activatable lighting elements for implementation with the motion sickness mitigation system.

For example, the fluid dynamics model generator 382 may be configured to utilize the physics-based fluid dynamics model to simulate a fluid as well as one or more objects provided in the fluid, according to the inertial state of the vehicle 300. In some implementations, the fluid dynamics model generator 382 may be configured to utilize a physics-based fluid dynamics model to simulate the one or more objects instead of the fluid, according to the inertial state of the vehicle 300. For a given container or vessel, a given viscosity of the fluid, and a given force (corresponding to the inertial state of the vehicle), the physics-based fluid dynamics model may simulate the fluid, the one or more objects, or the fluid and the one or more objects suspended in the fluid, according to known fluid dynamics models, for example, based on Bernoulli's principle and equation concerning fluid dynamics.

For example, the physics-based fluid dynamics model may simulate the fluid based on fluid animation techniques. Fluid animation aims to render realistic fluid visualizations from quantitative results of computational fluid dynamics (CFD) simulations. CFD is a diverse and mature field of research. Many CFD techniques share the same basic procedure and rely on computer assisted design (CAD) models to describe the physical boundaries (e.g., a container or vessel) of the fluid under study. Furthermore, partial differential equations (e.g., Navier-Stokes equations which describe the motion of fluids) may be utilized to describe the physics or motion of fluids and numerical methods may be used to solve the partial differential equations. In some implementations, the CFD model may divide the fluid under study by discretizing the fluid domain into a set of computational or discrete cells (e.g., nodes) to form a mesh. Several methods can be used to describe how cells interact with each other while abiding by the aforementioned partial differentiable equations. Examples include, but are not limited to, the finite element method, the finite volume method, etc. For example, a finite element analysis approach may be implemented to divide a container (e.g., a tube) into small elements (e.g., nodes) and the partial differentiable equations may be solved for each element. For example, CFD techniques may use a numerical solver to converge to an accurate approximation of the fluid dynamics. As yet another example, Euler equations, which describe the motion of a fluid in the absence of viscosity, may be used to model the motion of a fluid. The Euler equations are a simplified version of the Navier-Stokes equations and are based on the assumption that the fluid is inviscid. In contrast, the Navier-Stokes equations take into account viscous forces.

As described herein, the one or more containers or vessels to be used by the physics-based fluid dynamics model may be determined based on the configurations of the lighting elements that are to be used for visualizing the simulated fluid, the simulated one or more objects, or the simulated fluid and the one or more objects suspended in the fluid.

For example, the objects may include granules (e.g., sand), air bubbles, filament structures, fiber-like structures (e.g., seaweed), or other objects. The particular object to be utilized by the fluid dynamics model generator 382 may be selected via the fluid objects selector 386. The fluid objects selector 386 may be configured to automatically select or implement an object to be modeled by the fluid dynamics model generator 382 or the object may be selected via a user input.

As an example, when the lighting element selector 384 identifies that lighting elements from the front zone are activatable for purposes of implementing the motion sickness mitigation system while lighting elements from the rear zone are excluded as being activatable for purposes of implementing the motion sickness mitigation system, the fluid dynamics model generator 382 may be configured to utilize a physics-based fluid dynamics model to simulate the fluid according to the inertial state of the vehicle 300 and according to containers having shapes that correspond to the configuration of the one or more lighting elements that are provided in the front zone. For example, the front zone may include a first lighting element configuration on the dashboard which is linear and second and third lighting element configurations surrounding the left and right interior door handles, respectively, which are box-shaped. Therefore, the fluid dynamics model generator 382 may be configured to model fluid in a first container that is linear and in the form of a tube (corresponding to the first lighting element configuration) and to model fluid in a second container that is box-shaped and in the form of a tube (corresponding to the second and third lighting element configurations).

For example, the fluid dynamics model generator 382 may be configured to utilize the physics-based fluid dynamics model to simulate a fluid having a particular viscosity, according to the inertial state of the vehicle 300. For example, the fluid viscosity selector 388 may be configured to increase a viscosity of the fluid when implementing the fluid dynamics model in response to the motion of the vehicle 300 being greater than a threshold value. Increasing the viscosity of the fluid may be useful to more smoothly visualize the movement of the fluid via the lighting elements disposed in the interior of the vehicle 300. For example, the fluid viscosity selector 388 may select a viscosity value similar to that of the viscosity of water (e.g., 1.00 centipoise (cP)) as a default value. However, other viscosity values may be selected (e.g., 0.6 cP. 1.5 cP. 2.0 cP, 50 cP, 5,000 cP, etc.). In some implementations, a user may be enabled to change the viscosity value, for example, via a user interface, according to a user preference.

The on-board system 350 may communicate with a fluid visualization system 390 that may be integrated with the vehicle 300 or may be provided remotely from the vehicle 300. For example, the fluid visualization system 390 may be or may include a remote server. The fluid visualization system 390 may include one or more control circuits 392. In an embodiment, the one or more control circuits 392 may include one or more processors (e.g., microprocessors), one or more processing cores, a programmable logic circuit (PLC) or a programmable logic/gate array (PLA/PGA), a field programmable gate array (FPGA), an application specific integrated circuit (ASIC), or any other control circuit. In some implementations, the one or more control circuits 392 may be embodied as the one or more control circuits 352. That is, the one or more control circuits 352 of the on-board system 350 may perform the operations of the one or more control circuits 392.

In an embodiment, the fluid visualization system 390 may include a non-transitory computer-readable medium 394 (also referred to as memory 394). The non-transitory computer-readable medium 394 may be a memory device, also referred to as a data storage device, which may include an electronic storage device, a magnetic storage device, an optical storage device, an electromagnetic storage device, a semiconductor storage device, or any suitable combination thereof. The non-transitory computer-readable medium may form, e.g., a hard disk drive (HDD), a solid state drive (SDD) or solid state integrated memory, a random access memory (RAM), a read-only memory (ROM), an erasable programmable read-only memory (EPROM or Flash memory), a static random access memory (SRAM), dynamic random access memory (DRAM), a portable compact disc read-only memory (CD-ROM), a digital versatile disk (DVD), and/or a memory stick. In some implementations, the non-transitory computer-readable medium 394 may be embodied as the non-transitory computer-readable medium 354. That is, non-transitory computer-readable medium 354 of the on-board system 350 may perform the operations of the non-transitory computer-readable medium 394.

The fluid visualization system 390 may implement or otherwise provide services that facilitate motion sickness mitigation according to aspects of the disclosure. The fluid visualization system 390 may be in communication with various vehicle systems or sensors, for example via on-board system 350, for controlling one or more lighting elements of the vehicle 300 so as to cause the simulated fluid (as determined by the fluid dynamics simulations system 370) to be visualized within an interior of the vehicle using one or more lighting elements from among a plurality of activatable lighting elements of the vehicle 300. The fluid visualization system 390 may store various data in non-transitory computer-readable medium 394 for use in controlling a state of the lighting elements (e.g., light intensity values, node density threshold values, etc.).

The fluid visualization system 390 may be configured to visualize the simulated fluid as determined by the fluid dynamics simulation system 370 within an interior of the vehicle 300 using one or more lighting elements from among a plurality of activatable lighting elements of the vehicle 300. For example, the fluid visualization system 390 may include a lighting element controller 396 which is configured to visualize the simulated fluid by activating and/or deactivating one or more lighting elements provided in the interior of the vehicle 300 including dashboard lighting elements 141, door lighting elements 142, display screen lighting elements 143, seat lighting elements 144, screen bezel lighting elements 145, window lighting elements 146, console lighting elements 147, and the like.

For example, the fluid visualization system 390 may include a light intensity selector 398 which is configured to visualize the simulated fluid by selecting or setting a light intensity for one or more lighting elements provided in the interior of the vehicle 300 based on the simulated fluid. For example, where the model output indicates a node density value is greater than a first threshold level at a particular node of the container, the light intensity selector 398 may be configured to increase an intensity of a corresponding lighting element, and where the model output indicates a node density value is less than a second threshold level at a particular node of the container, the light intensity selector 398 may be configured to decrease an intensity of a corresponding lighting element. For example, where the model output indicates a node density value is between the first threshold level and the second threshold level at a particular node of the container, the light intensity selector 398 may be configured to maintain an intensity of a corresponding lighting element at a default level.

Figure 4A:
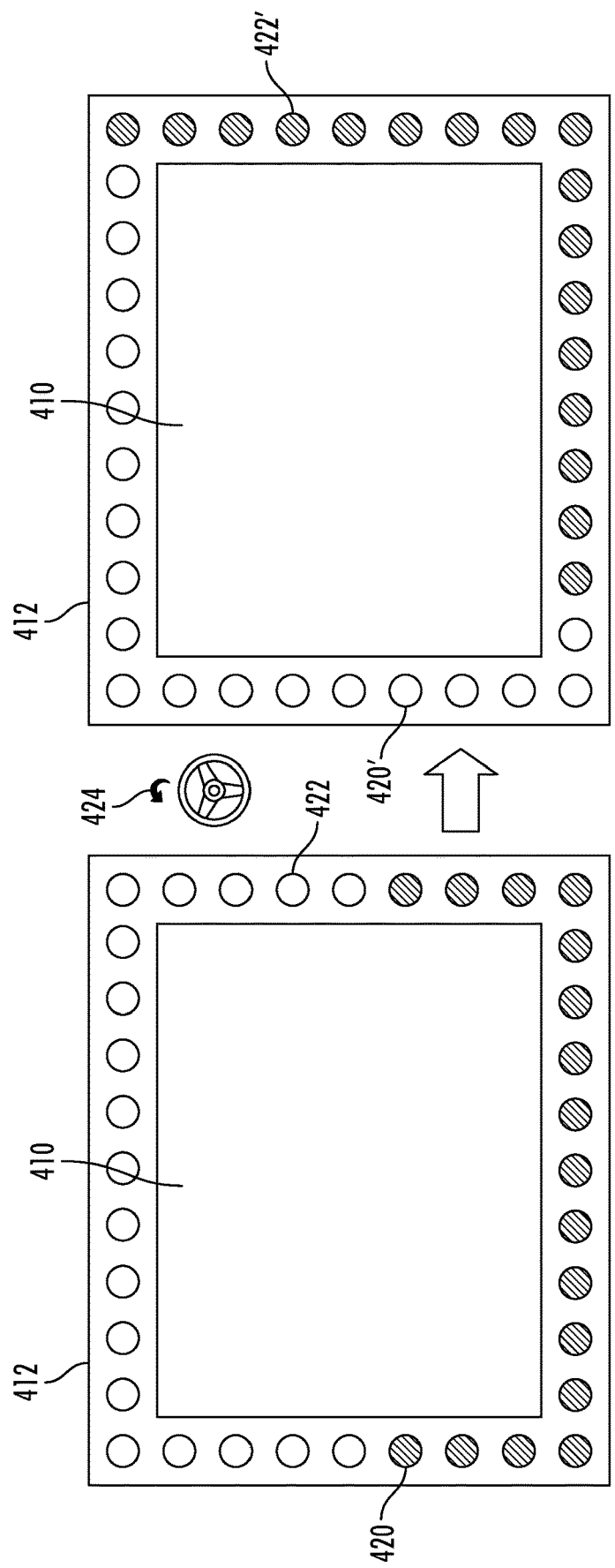
FIGS. 4A-4C illustrate example visualizations of a simulated fluid using lighting elements of the vehicle, according to example embodiments of the disclosure.
Figure 4B:
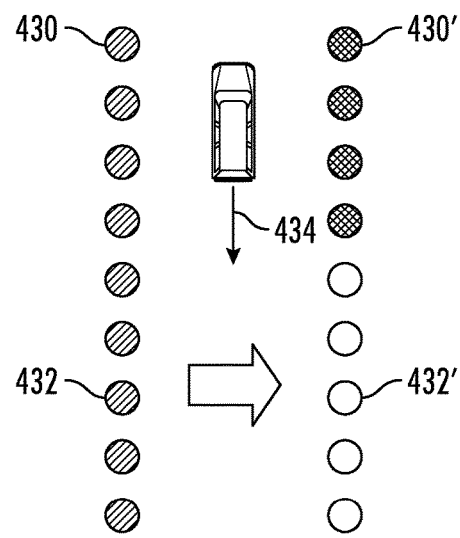
Figure 4C:
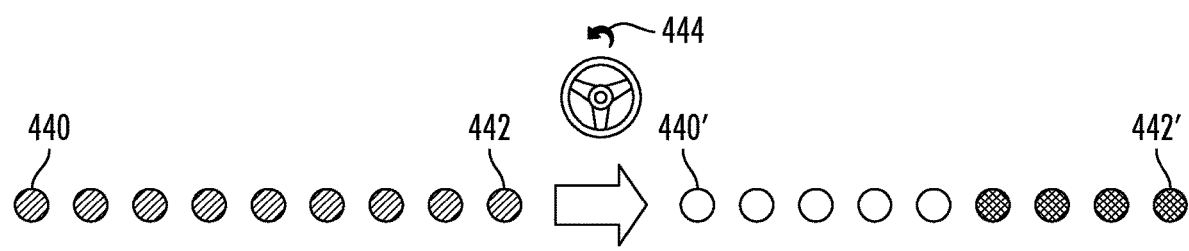

Referring to FIGS. 4A-4C, example visualizations of a simulated fluid using lighting elements of the vehicle are illustrated, according to example embodiments of the disclosure. Referring to the example of FIG. 4A, lighting elements are disposed in a rectangular manner on a bezel 412 of a display screen 410 which can be provided in the vehicle 300 similar to that shown in FIG. 2A. The fluid dynamics model generator 382 may be configured to model a state of a fluid based on an inertial state of the vehicle 300 by simulating a vessel or container having the same or similar shape as the lighting elements disposed in the rectangular manner on the bezel 412. For example, the vessel or container utilized for simulating the state of the fluid according to the inertial state of the vehicle may have the same or similar shape as the lighting elements but need not have the same dimensions (e.g., in terms of length, width, depth, etc.) as the configuration of the lighting elements. The fluid dynamics model generator 382 may be configured to represent the configuration of the lighting elements as a network of nodes or as a mesh topology. The fluid dynamics model generator 382 may be configured to simulate the motion of the fluid in the container, for example with respect to each node, based on the inertial state of the vehicle.

In some implementations, where the model output indicates fluid is present in a particular node of the container, a corresponding lighting element may be activated, and where the model output indicates air is present in a particular node (e.g., the fluid has left the node), a corresponding lighting element may be deactivated.

In some implementations, where the model output indicates a node density value is greater than a first threshold level at a particular node of the container, an intensity of a corresponding lighting element may be increased, and where the model output indicates a node density value is less than a second threshold level at a particular node of the container, an intensity of a corresponding lighting element may be decreased. For example, where the model output indicates a node density value is between the first threshold level and the second threshold level at a particular node of the container, an intensity of a corresponding lighting element may be maintained at a default level.

Referring again to the example of FIG. 4A, for a first inertial state of the vehicle 300 (e.g., on a flat road and having a substantially constant speed), various lighting elements 420 may be activated in a symmetric manner (e.g., equal number of lighting elements 420 activated on the sides of the bezel 412) and various lighting elements 422 may be deactivated in a symmetric manner (e.g., equal number of lighting elements 422 deactivated on the sides of the bezel 412). In response to a left turn by the vehicle 300 (indicated by arrow 424) the vehicle 300 may enter a second inertial state (e.g., with centrifugal forces acting on the vehicle 300). Based on the second inertial state of the vehicle 300, the fluid dynamics model generator 382 may be configured to model a state of a fluid such that the fluid "sloshes" to one side of the container utilized in the model which corresponds to the configuration of the lighting elements. Here, the sloshing effect of the fluid occurs based on the centrifugal forces acting on the vehicle 300 during the turn and thus the model reflects the inertial state of the vehicle 300. Corresponding lighting elements disposed about the bezel 412 may be activated and deactivated to reflect the simulated fluid. For example, some lighting elements 422' which were previously deactivated may be activated and some lighting elements 420' which were previously activated may be deactivated, such that activation and deactivation of the lighting elements act as a visual cue which is consistent with what the occupants in the vehicle 300 feel, mitigating their susceptibility to motion sickness.

Similarly, in the example of FIG. 4B for a first inertial state of the vehicle 300 (e.g., on a flat road and having a substantially constant speed), various lighting elements including lighting elements 430 and 432 are activated and are disposed along a longitudinal direction of the vehicle (e.g., along the floor or along a door). In response to a braking action by the vehicle 300 (indicated by arrow 434) the vehicle 300 may enter a second inertial state (e.g., with deceleration forces acting on the vehicle 300). Based on the second inertial state of the vehicle 300, the fluid dynamics model generator 382 may be configured to model a state of a fluid such that the fluid "sloshes" to one side of the container utilized in the model which corresponds to the configuration of the lighting elements. In the example of FIG. 4B, some lighting elements 432' which were previously activated may be deactivated and some lighting elements 430' which were previously activated with a default lighting intensity level may remain activated but have a higher intensity lighting level based on an increased density of the corresponding node in the model, such that activation and deactivation of the lighting elements act as a visual cue which is consistent with what the occupants in the vehicle 300 feel, mitigating their susceptibility to motion sickness. The example of FIG. 4B may also apply in a circumstance where a state of the vehicle 300 changes from being situated on a flat and level road to descending down a hill or being parked on a hill in a declined manner.

Similarly, in the example of FIG. 4C for a first inertial state of the vehicle 300 (e.g., on a flat road and having a substantially constant speed), various lighting elements including lighting elements 440 and 442 are activated and are disposed along a transverse direction of the vehicle (e.g., along the dashboard in a left to right manner). In response to a turning action by the vehicle 300 (indicated by arrow 434) the vehicle 300 may enter a second inertial state (e.g., with centrifugal forces acting on the vehicle 300). Based on the second inertial state of the vehicle 300, the fluid dynamics model generator 382 may be configured to model a state of a fluid such that the fluid "sloshes" to one side of the container utilized in the model which corresponds to the configuration of the lighting elements. In the example of FIG. 4C, some lighting elements 440' which were previously activated may be deactivated and some lighting elements 442' which were previously activated with a default lighting intensity level may remain activated but have a higher intensity lighting level based on an increased density of the at the corresponding node in the model, such that activation and deactivation of the lighting elements act as a visual cue which is consistent with what the occupants in the vehicle 300 feel, mitigating their susceptibility to motion sickness.

Figure 5A:
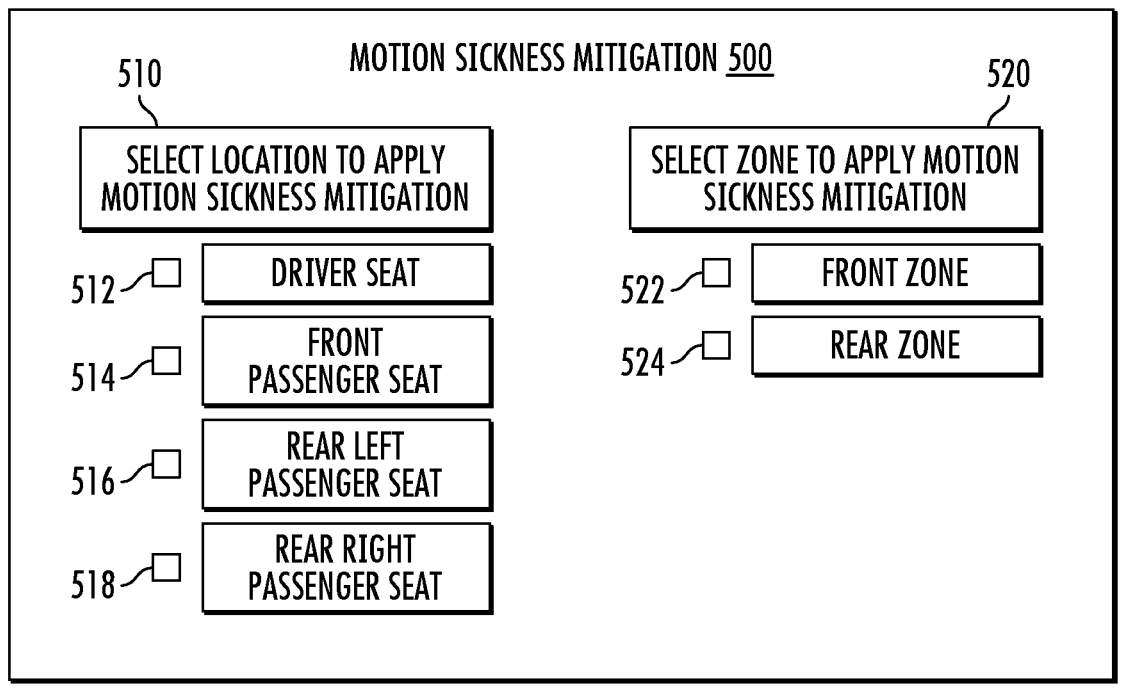
FIGS. 5A-5B illustrate example user interfaces for operating the motion sickness mitigation system, according to example embodiments of the disclosure.
Figure 5B:
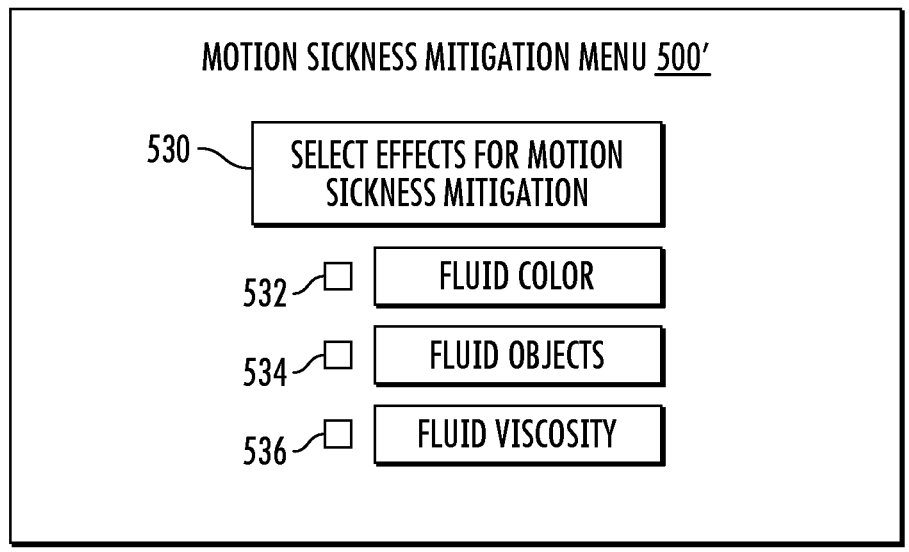

As mentioned above, various setting with respect to the motion sickness mitigation system may be controlled by an occupant of the vehicle. For example, the motion sickness mitigation system may be implemented as part of an active comfort system (e.g., as part of a luxury package) that is controllable by a user. FIGS. 5A-5B illustrate example user interfaces for operating the motion sickness mitigation system, according to example embodiments of the disclosure.

FIG. 5A illustrates a first motion sickness mitigation user interface 500 including a plurality of user interface elements that can be used to select one or more areas within the vehicle to which the motion sickness mitigation system may be applied. For example, a user may be enabled to select or identify a particular location within the vehicle to apply motion sickness mitigation by selecting user interface element 510. The user may then identify or select particular seats within the vehicle to apply motion sickness mitigation by selecting one or more of user interface elements 512, 514, 516, and 518 (e.g., via a touch input to a touch screen, cursor selection, voice, input, etc.). FIG. 5A is merely an example and a vehicle may include more or fewer seats than the example of FIG. 5A. For example, a user may be enabled to select or identify a particular zone within the vehicle to apply motion sickness mitigation by selecting user interface element 520. The user may then identify or select a particular zone within the vehicle (e.g., a front zone and/or a rear zone) to apply motion sickness mitigation by selecting one or more of user interface elements 522 and 524. FIG. 5A is merely an example and a vehicle may include more or fewer zones than the example of FIG. 5A.

FIG. 5B illustrates a second motion sickness mitigation user interface 500' including a plurality of user interface elements that can be used to select particular options with respect to the execution of the motion sickness mitigation system. For example, a user may be enabled to select one or more effects to be applied for motion sickness mitigation by selecting user interface element 530. For example, the user may select a particular fluid color to be visually represented via the lighting elements within the vehicle to apply motion sickness mitigation by selecting user interface element 532. For example, a submenu may be displayed with a plurality of color options from which the user can select a particular color. For example, the user may select a particular fluid object to be included in the fluid and represented via the lighting elements within the vehicle to apply motion sickness mitigation by selecting user interface element 534. For example, a submenu may be displayed with a plurality of different objects (e.g., granules, air bubbles, filament structures, fiber-like structures, or other objects which are suspended in the fluid), from which the user can select a particular object. For example, the user may select a particular fluid viscosity for the fluid and represented via the lighting elements within the vehicle to apply motion sickness mitigation by selecting user interface element 536. For example, a submenu may be displayed with a plurality of different viscosity values and/or substances having similar viscosity values, from which the user can select a particular viscosity.

Example Methods for Motion Sickness Mitigation

FIGS. 6A-6D illustrate flowchart diagrams for various methods for implementing motion sickness mitigation, according to example embodiments of the disclosure.

Figure 6A:
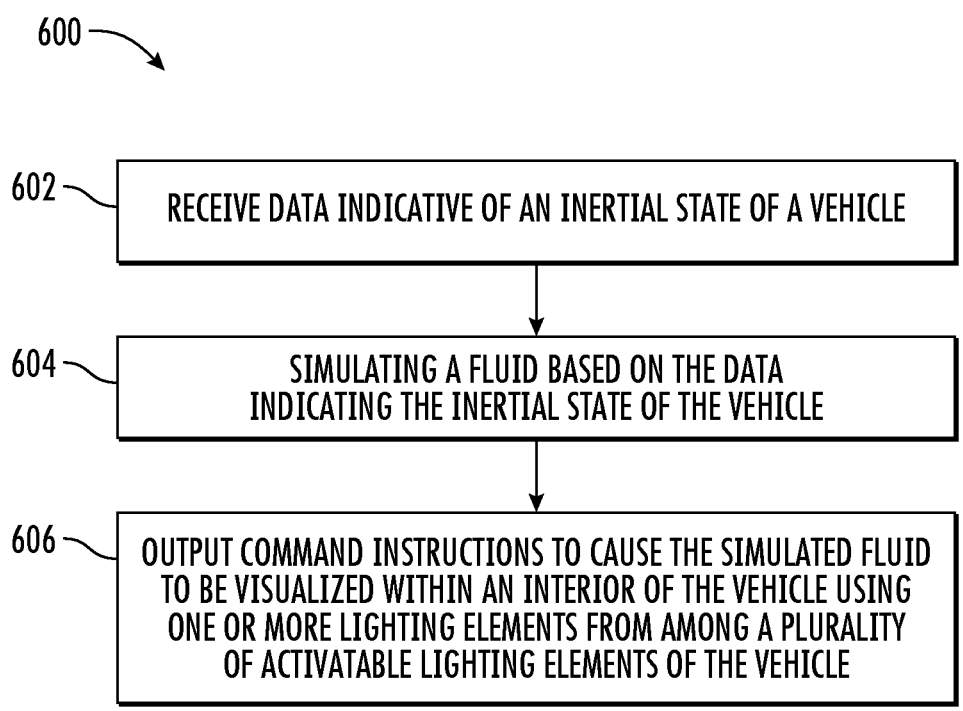
FIGS. 6A-6D illustrate flowchart diagrams for various methods for implementing motion sickness mitigation, according to example embodiments of the disclosure.

FIG. 6A depicts a flow diagram that illustrates a method 600 for motion sickness mitigation. In an embodiment, the method 600 may be performed by the control circuit 352 of the on-board system 350 and/or the control circuit(s) 372 of fluid dynamics simulation system 370 and/or the control circuit(s) 392 of fluid visualization system 390 of FIG. 3. In another embodiment, the method 600 may be performed by one or more of the control circuits 715, 815, 915 of the computing system 700 of FIG. 7. One or more portions of the method 600 may be implemented as an algorithm on the hardware components of the devices described herein. For example, the operations of method 600 may be implemented as operations/instructions that are executable by computing hardware.

Although FIG. 6A depicts operations performed in a particular order for purposes of illustration and discussion, the methods of the disclosure are not limited to the particularly illustrated order or arrangement. The various operations of the method 600 may be omitted, rearranged, combined, and/or adapted in various ways without deviating from the scope of the disclosure.

In an embodiment, the method 600 may begin with or otherwise include an operation 602, in which a computing system (e.g., the systems 110, 350, 370, and/or 700) receives, via one or more sensors of a vehicle (e.g., 200A, 200B, 300), data indicative of an inertial state of the vehicle (e.g., 200A, 200B, 300). For example, the vehicle may be an autonomous vehicle. As discussed above, the data may include one or more of IMU data 121, camera data 122, speed sensor data 123, LIDAR data 124, RADAR data 125, magnetometer data 126, inclinometer data 127, position data 128, and the like. For example, the data indicative of the inertial state may include at least one of: (i) acceleration data of the vehicle, (ii) angular motion data of the vehicle, (iii) speed data of the vehicle, (iv) pitch angle data of the vehicle, (v) roll angle data of the vehicle, or (vi) yaw angle data of the vehicle. For example, the control circuit may receive the data indicating the inertial state of the vehicle from at least one of: (i) one or more accelerometers, (ii) one or more gyroscopes, (iii) one or more magnetometers, (iv) one or more inclinometers, (v) one or more cameras, (vi) one or more LIDAR sensors, (vii) one or more RADAR sensors, (viii) one or more wheel speed sensors, or (ix) one or more global navigation positioning sensors.

Referring still to FIG. 6A, the method 600 may, in an embodiment, include an operation 604, in which the computing system (e.g., the systems 110, 350, 370, and/or 700) simulates a fluid based on the data indicating the inertial state of the vehicle (e.g., 200A, 200B, 300). For example, a fluid dynamics simulation system (e.g., systems 110, 350, 370) may be configured to utilize a physics-based fluid dynamics model to simulate a fluid based on the data indicating the inertial state of the vehicle (e.g., 200A, 200B, 300). In an embodiment, the fluid dynamics simulation system (e.g., systems 110, 350, 370) may simulate the fluid based on the data indicating the inertial state of the vehicle (e.g., 200A, 200B, 300) by modeling fluid dynamics associated with the fluid and one or more objects in the fluid, according to the inertial state of the vehicle (e.g., 200A, 200B, 300). The objects may include one or more of: (i) granules, (ii) air bubbles, (iii) filaments, or (iv) fiber-like structures.

In some implementations, the fluid dynamics simulation system (e.g., systems 110, 350, 370) may be configured to utilize a physics-based fluid dynamics model to simulate the fluid according to the inertial state of the vehicle (e.g., 200A, 200B, 300) and according to a known or preset vessel or container having a shape that corresponds to an arrangement or configuration of lighting elements that are provided in the vehicle (e.g., 200A, 200B, 300). That is, the fluid containers or vessels used by the model implemented by the fluid dynamics simulation system (e.g., systems 110, 350, 370) are configured to match the lighting element configurations in the vehicle (e.g., 200A, 200B, 300) to be utilized for visualizing the simulated fluid, as described herein. For example, non-transitory computer-readable medium 374 and/or non-transitory computer-readable medium 354 may store in a database or look-up table a mapping between a lighting element configuration and a specified container or vessel used by the model implemented by the fluid dynamics simulation system (e.g., systems 110, 350, 370). For example, a linear arrangement of lighting elements (e.g., along a seat, door, dashboard, etc.) may correspond to a first container used by the fluid dynamics model that is linear and in the form of a tube. For example, a box-shaped arrangement of lighting elements (e.g., lighting elements provided on a bezel disposed around a display screen, a configuration of lighting elements that surround an interior door handle, etc.) may correspond to a second container used by the fluid dynamics model that is also box-shaped and in the form of a tube. Thus, each of the configurations of the lighting elements (e.g., by location) may be mapped to a separate or common container in the fluid dynamics model, for example, based on a shape of the configuration of the lighting elements.

In an embodiment, when simulating the fluid, the computing system may determine one or more lighting elements from among the plurality of activatable lighting elements to be selectively deactivated, activated, or both, to simulate the fluid based on the data indicating the inertial state of the vehicle.

In an embodiment, when simulating the fluid, the computing system may determine the one or more lighting elements from among the plurality of activatable lighting elements to be selectively deactivated, activated, or both based on at least one of a location of an occupant within the vehicle or based on a viewing direction of the occupant.

In an embodiment, the control circuit may receive data indicating a location of an occupant within the vehicle and determine the one or more lighting elements from among the plurality of activatable lighting elements to visualize the simulated fluid based on the location of the occupant such that the visualization of the simulated fluid is in a field of view of the occupant.

In an embodiment, the simulated fluid may be based on a viscosity of the fluid. For example, the method 600 may include an operation in which the computing system determines, based on a default setting or a user setting, a viscosity of the fluid to model the fluid dynamics associated with the fluid. The computing system can determine and visualize the simulated fluid based on the viscosity of the fluid, as described herein.

The method 600 of FIG. 6A may, in an embodiment, include an operation 606, in which the computing system (e.g., the systems 110, 350, 370, and/or 700) outputs command instructions to cause the simulated fluid to be visualized within an interior of the vehicle (e.g., 200A, 200B, 300) using one or more lighting elements from among a plurality of activatable lighting elements of the vehicle (e.g., 200A, 200B, 300). As described herein, the plurality of activatable lighting elements may be provided at, at least one of: (i) a dashboard of the vehicle, (ii) one or more seats of the vehicle, (iii) one or more door panels of the vehicle, (iv) one or more display screens of the vehicle, (v) one or more windows of the vehicle, or (vi) one or more consoles of the vehicle. For example, a fluid visualization system (e.g., systems 130, 350, 390) may be configured to utilize (e.g., activate and/or deactivate) one or more lighting elements provided in the interior of the vehicle (e.g., 200A, 200B, 300) including dashboard lighting elements 141, door lighting elements 142, display screen lighting elements 143, seat lighting elements 144, screen bezel lighting elements 145, window lighting elements 146, console lighting elements 147, and the like.

The fluid visualization system may output command instructions to activate, deactivate, or both, the one or more lighting elements from among the plurality of activatable lighting elements to visually represent the fluid within the interior of the vehicle. For example, the plurality of activatable lighting elements may be provided in an array, as described herein. The command instructions may be configured to deactivate, activate, or both, the one or more lighting elements of the plurality of activatable lighting elements provided in the array to visualize the simulated fluid.

In an embodiment, to simulate the fluid the method 600 may include determining movement of suspended air bubbles or other objects (e.g., granules, filaments, fiber-like structures, etc.) in the fluid based on the data indicating the inertial state of the vehicle. The command instructions may be configured to cause the one or more lighting elements from among the plurality of activatable lighting elements to be controlled to represent the movement of the suspended air bubbles in the fluid based on the inertial state of the vehicle.

Figure 6B:
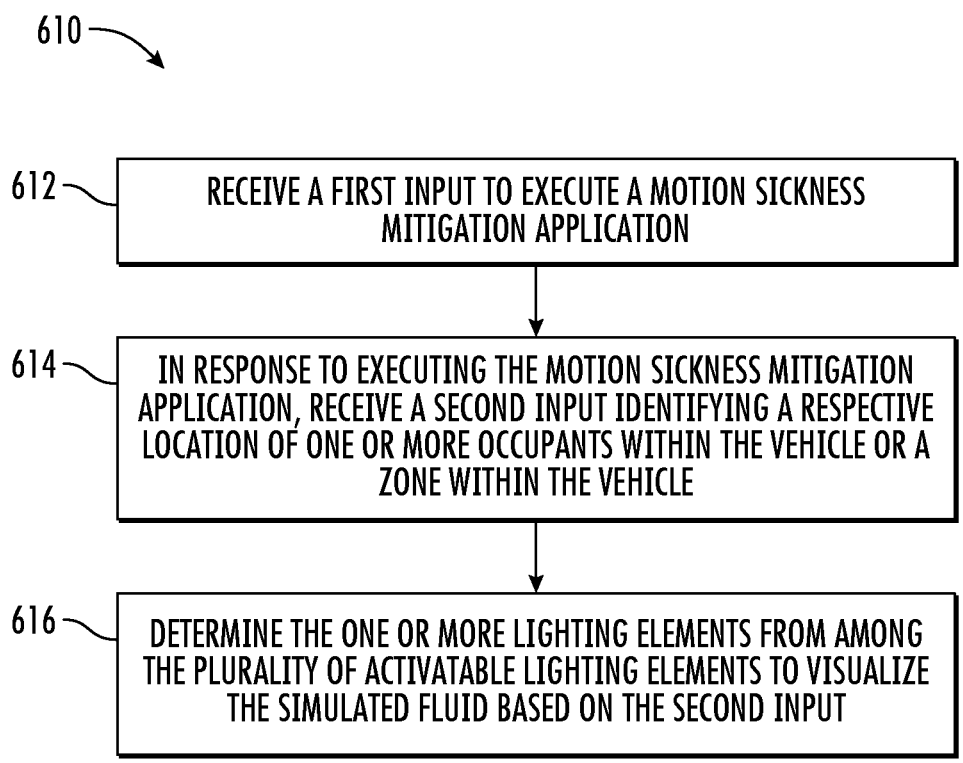

FIG. 6B depicts a flow diagram that illustrates a method 610 for motion sickness mitigation. In an embodiment, the method 610 may be performed by the control circuit 352 of the on-board system 350 and/or the control circuit(s) 372 of fluid dynamics simulation system 370 and/or the control circuit(s) 392 of fluid visualization system 390 of FIG. 3. In another embodiment, the method 610 may be performed by one or more of the control circuits 715, 815, 915 of the computing system 700 of FIG. 7. One or more portions of the method 610 may be implemented as an algorithm on the hardware components of the devices described herein. For example, the operations of method 610 may be implemented as operations/instructions that are executable by computing hardware.

Although FIG. 6B depicts operations performed in a particular order for purposes of illustration and discussion, the methods of the disclosure are not limited to the particularly illustrated order or arrangement. The various operations of the method 610 may be omitted, rearranged, combined, and/or adapted in various ways without deviating from the scope of the disclosure.

In an embodiment, the method 610 may begin with or otherwise include an operation 612, in which a computing system (e.g., the systems 110, 350, 370, and/or 700) receives a first input to execute a motion sickness mitigation application. For example, the motion sickness mitigation application may be stored in any of non-transitory computer readable medium 354, 374, 394 and be executed in response to the computing system receiving a first input. For example, the first input may be received via a voice input, touch input (e.g., through a user interface), and the like. The motion sickness mitigation application may be implemented as part of an active comfort system that enables a user to select various settings. As another example, the motion sickness mitigation application may be executed automatically by the vehicle (e.g., 200A, 200B, 300) in response to detecting the presence of a particular occupant of the vehicle (e.g., 200A, 200B, 300). For example, the occupant may have a user preference or default setting associated with the occupant and the vehicle (e.g., 200A, 200B, 300) such that the vehicle (e.g., 200A, 200B, 300) automatically executes the motion sickness mitigation application when determining that the occupant is located within the vehicle (e.g., 200A, 200B, 300).

Referring still to FIG. 6B, the method 610 may, in an embodiment, include an operation 614, in which the computing system (e.g., the systems 110, 350, 370, and/or 700), in response to executing the motion sickness application, receives a second input identifying a respective location of one or more occupants within the vehicle (e.g., 200A, 200B, 300) or a zone within the vehicle (e.g., 200A, 200B, 300). For example, a particular location or zone for which the motion sickness mitigation system is to be applied to may be specified as the second input according to a user input (e.g., via the example user interface of FIG. 5A, via a voice input, touch input, etc.). As another example, a particular location or zone for which the motion sickness mitigation system is to be applied to may be specified as the second input according to the vehicle detecting a location of occupants in the vehicle (e.g., via seat detection systems including via weight sensors, camera detection, and the like).

Referring still to FIG. 6B, the method 610 may, in an embodiment, include an operation 616, in which the computing system (e.g., the systems 110, 350, 370, and/or 700), determines the one or more lighting elements from among the plurality of activatable lighting elements to visualize the simulated fluid based on the second input. For example, when a front zone is identified via the second input and a rear zone is not identified via the second input, the computing system may include lighting elements from the front zone as potential activatable lighting elements to visualize the simulated fluid. For example, when a front zone is identified via the second input and a rear zone is not identified via the second input, the computing system may exclude lighting elements from the rear zone as potential activatable lighting elements to visualize the simulated fluid.

Figure 6C:
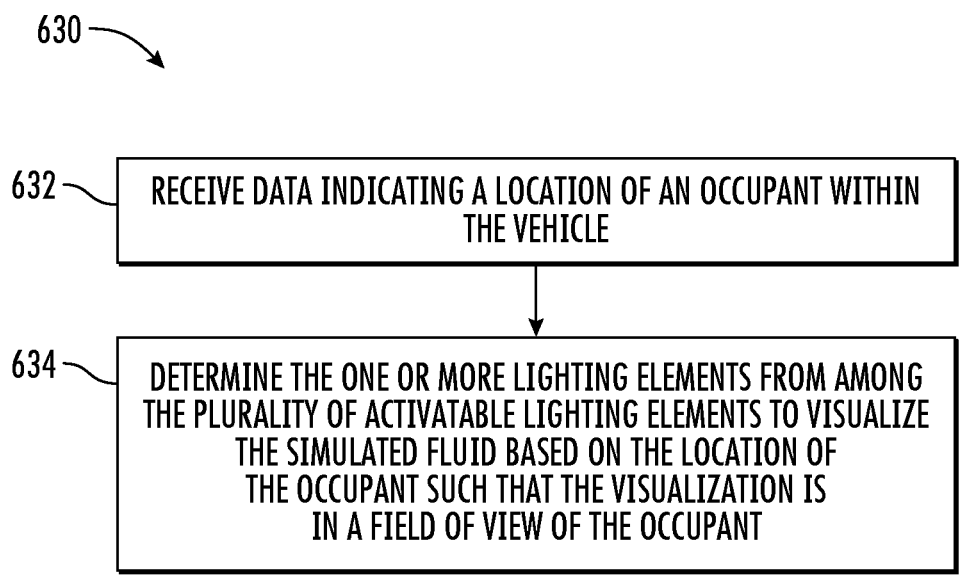

FIG. 6C depicts a flow diagram that illustrates a method 630 for motion sickness mitigation. In an embodiment, the method 630 may be performed by the control circuit 352 of the on-board system 350 and/or the control circuit(s) 372 of fluid dynamics simulation system 370 and/or the control circuit(s) 392 of fluid visualization system 390 of FIG. 3. In another embodiment, the method 630 may be performed by one or more of the control circuits 715, 815, 915 of the computing system 700 of FIG. 7. One or more portions of the method 630 may be implemented as an algorithm on the hardware components of the devices described herein. For example, the operations of method 630 may be implemented as operations/instructions that are executable by computing hardware.

Although FIG. 6C depicts operations performed in a particular order for purposes of illustration and discussion, the methods of the disclosure are not limited to the particularly illustrated order or arrangement. The various operations of the method 630 may be omitted, rearranged, combined, and/or adapted in various ways without deviating from the scope of the disclosure.

In an embodiment, the method 630 may begin with or otherwise include an operation 632, in which a computing system (e.g., the systems 110, 350, 370, and/or 700) receives data indicating a location of an occupant within the vehicle (e.g., 200A, 200B, 300). For example, the computing system (e.g., the systems 110, 350, 370, and/or 700) may receive data indicating a particular location or zone for which the motion sickness mitigation system is to be applied according to a user input (e.g., via the example user interface of FIG. 5A, via a voice input, touch input, etc.). As another example, the computing system (e.g., the systems 110, 350, 370, and/or 700) may receive data indicating a particular location or zone for which the motion sickness mitigation system is to be applied according to sensor data (e.g., the vehicle (e.g., 200A, 200B, 300) detecting a location of occupants in the vehicle (e.g., 200A, 200B, 300) via seat detection systems including via weight sensors, via camera detection, and the like).

Referring still to FIG. 6C, the method 630 may, in an embodiment, include an operation 634, in which the computing system (e.g., the systems 110, 350, 370, and/or 700) determines the one or more lighting elements from among the plurality of activatable lighting elements to visualize the simulated fluid based on the location of the occupant such that the visualization of the simulated fluid is in a field of view of the occupant. For example, when the data indicates one or more occupants are located in a front zone and no occupants are located in a rear zone, the computing system may include lighting elements from the front zone as potential activatable lighting elements to visualize the simulated fluid. For example, when the data indicates one or more occupants are located in a front zone and no occupants are located in a rear zone, the computing system may exclude lighting elements from the rear zone as potential activatable lighting elements to visualize the simulated fluid.

Figure 6D:
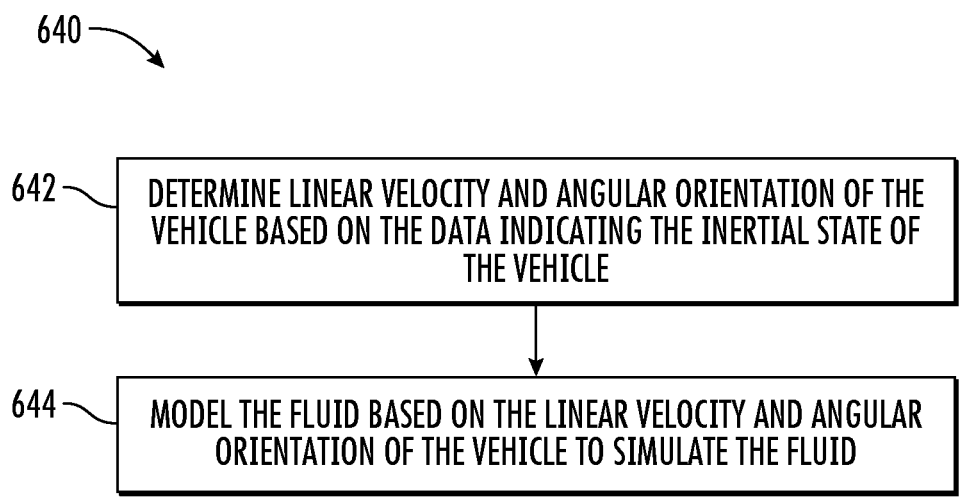

FIG. 6D depicts a flow diagram that illustrates a method 640 for motion sickness mitigation. In an embodiment, the method 640 may be performed by the control circuit 352 of the on-board system 350 and/or the control circuit(s) 372 of fluid dynamics simulation system 370 and/or the control circuit(s) 392 of fluid visualization system 390 of FIG. 3. In another embodiment, the method 640 may be performed by one or more of the control circuits 715, 815, 915 of the computing system 700 of FIG. 7. One or more portions of the method 640 may be implemented as an algorithm on the hardware components of the devices described herein. For example, the operations of method 640 may be implemented as operations/instructions that are executable by computing hardware.

Although FIG. 6D depicts operations performed in a particular order for purposes of illustration and discussion, the methods of the disclosure are not limited to the particularly illustrated order or arrangement. The various operations of the method 640 may be omitted, rearranged, combined, and/or adapted in various ways without deviating from the scope of the disclosure.

In an embodiment, the method 640 may begin with or otherwise include an operation 642, in which a computing system (e.g., the systems 110, 350, 370, and/or 700) determines whether the vehicle's (e.g., 200A, 200B, 300) linear velocities and/or angular orientations change over time, based on the data indicating the inertial state of the vehicle (e.g., 200A, 200B, 300). For example, the computing system (e.g., the systems 110, 350, 370, and/or 700) may receive data indicating the vehicle (e.g., 200A, 200B, 300) is turning based on the data indicating the inertial state of the vehicle (e.g., 200A, 200B, 300).

Referring still to FIG. 6D, the method 640 may, in an embodiment, include an operation 644, in which the computing system (e.g., the systems 110, 350, 370, and/or 700) models the fluid based on whether the vehicle's (e.g., 200A, 200B, 300) linear velocities and/or angular orientations change over time to simulate the fluid. For example, as the vehicle turns in a first direction, the computing system (e.g., the systems 110, 350, 370, and/or 700) may model or simulate the fluid based on how the vehicle's linear velocities and angular orientations change over time based on how the vehicle's direction changes over time. For example, as the vehicle turns in a left direction, the computing system (e.g., the systems 110, 350, 370, and/or 700) may model or simulate the fluid based on how the vehicle's linear velocities and angular orientations change over time due to the direction of the turn such that in the simulation the fluid is acted on by a centrifugal force. For example, when the container or vessel that is used to model the fluid is linear or partly linear, the simulation may indicate the turning action of the vehicle causes the fluid to slosh in a direction opposite to the turn. For example, FIGS. 4A and 4C are examples illustrating the activation and deactivation of various lighting elements to visualize the simulated fluid, based on how the vehicle's linear velocities and angular orientations change over time based on how the vehicle's direction changes over time (during the left turn).

For example, as the vehicle turns in a first direction, the command instructions are configured to deactivate, activate, or both, a first subset of the plurality of activatable lighting elements to visualize the simulated fluid, based on how the vehicle's linear velocities and angular orientations change over time due to the vehicle turning in the first direction, and as the vehicle turns in a second direction, the command instructions are configured to deactivate, activate, or both, a second subset of the plurality of activatable lighting elements to visualize the simulated fluid, based on how the vehicle's linear velocities and angular orientations change over time due to the vehicle turning in the second direction.

Example Computing Systems

Figure 7:
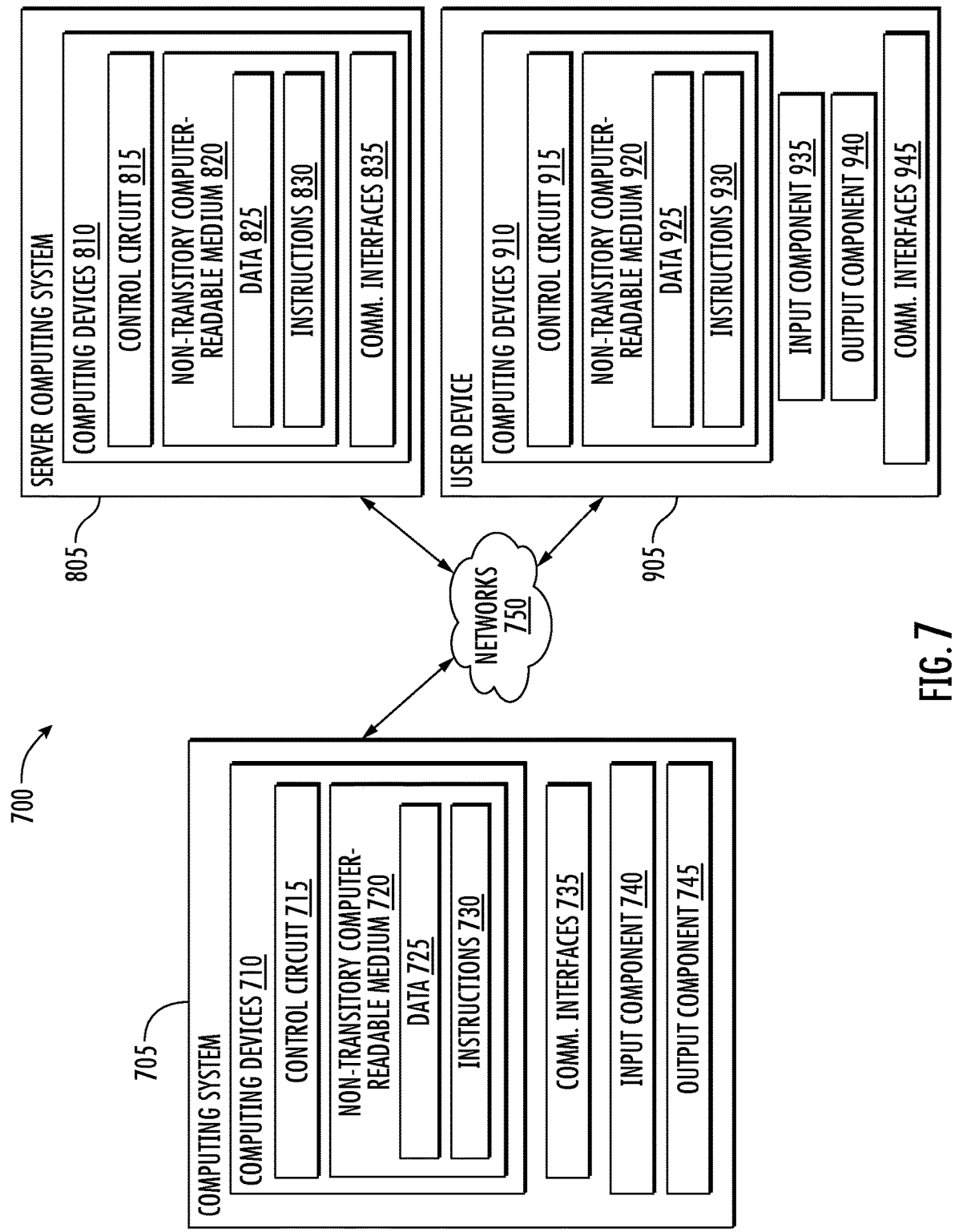
FIG. 7 illustrates a block diagram of computing systems, according to example embodiments of the disclosure.

FIG. 7 illustrates a block diagram of an example computing system 700 according to an embodiment hereof. The system 700 includes a computing system 705 (e.g., a computing system onboard a vehicle), a server computing system 805 (e.g., a remote computing system, cloud computing platform), and a user device 905 that are communicatively coupled over one or more networks 750.

The computing system 705 may include one or more computing devices 710 or circuitry. For instance, the computing system 705 may include a control circuit 715 and a non-transitory computer-readable medium 720, also referred to herein as memory. In an embodiment, the control circuit 715 may include one or more processors (e.g., microprocessors), one or more processing cores, a programmable logic circuit (PLC) or a programmable logic/gate array (PLA/PGA), a field programmable gate array (FPGA), an application specific integrated circuit (ASIC), or any other control circuit. In some implementations, the control circuit 715 may be part of, or may form, a vehicle control unit (also referred to as a vehicle controller) that is embedded or otherwise disposed in a vehicle (e.g., a Mercedes-Benz® car or van). For example, the vehicle controller may be or may include an infotainment system controller (e.g., an infotainment head-unit), a telematics control unit (TCU), an electronic control unit (ECU), a central powertrain controller (CPC), a charging controller, a central exterior & interior controller (CEIC), a zone controller, or any other controller. In an embodiment, the control circuit 715 may be programmed by one or more computer-readable or computer-executable instructions stored on the non-transitory computer-readable medium 720.

In an embodiment, the non-transitory computer-readable medium 720 may be a memory device, also referred to as a data storage device, which may include an electronic storage device, a magnetic storage device, an optical storage device, an electromagnetic storage device, a semiconductor storage device, or any suitable combination thereof. The non-transitory computer-readable medium 720 may form, e.g., a hard disk drive (HDD), a solid state drive (SDD) or solid state integrated memory, a random access memory (RAM), a read-only memory (ROM), an erasable programmable read-only memory (EPROM or Flash memory), a static random access memory (SRAM), dynamic random access memory (DRAM), a portable compact disc read-only memory (CD-ROM), a digital versatile disk (DVD), and/or a memory stick.

The non-transitory computer-readable medium 720 may store information that may be accessed by the control circuit 715. For instance, the non-transitory computer-readable medium 720 (e.g., memory devices) may store data 725 that may be obtained, received, accessed, written, manipulated, created, and/or stored. The data 725 may include, for instance, any of the data or information described herein. In some implementations, the computing system 705 may obtain data from one or more memories that are remote from the computing system 705.

The non-transitory computer-readable medium 720 may also store computer-readable instructions 730 that may be executed by the control circuit 715. The instructions 730 may be software written in any suitable programming language or may be implemented in hardware. The instructions may include computer-readable instructions, computer-executable instructions, etc. As described herein, in various embodiments, the terms "computer-readable instructions" and "computer-executable instructions" are used to describe software instructions or computer code configured to carry out various tasks and operations. In various embodiments, if the computer-readable or computer-executable instructions form modules, the term "module" refers broadly to a collection of software instructions or code configured to cause the control circuit 715 to perform one or more functional tasks. The modules and computer-readable/executable instructions may be described as performing various operations or tasks when the control circuit 715 or other hardware component is executing the modules or computer-readable instructions.

The instructions 730 may be executed in logically and/or virtually separate threads on the control circuit 715. For example, the non-transitory computer-readable medium 720 may store instructions 730 that when executed by the control circuit 715 cause the control circuit 715 to perform any of the operations, methods and/or processes described herein. In some cases, the non-transitory computer-readable medium 720 may store computer-executable instructions or computer-readable instructions, such as instructions to perform at least a portion of the methods of FIGS. 6A-6D.

The computing system 705 may include one or more communication interfaces 735. The communication interfaces 735 may be used to communicate with one or more other systems. The communication interfaces 735 may include any circuits, components, software, etc. for communicating via one or more networks (e.g., networks 750). In some implementations, the communication interfaces 735 may include for example, one or more of a communications controller, receiver, transceiver, transmitter, port, conductors, software and/or hardware for communicating data/information.

The computing system 705 may also include one or more user input components 740 that receives user input. For example, the user input component 740 may be a touch-sensitive component (e.g., a touch-sensitive display screen or a touch pad) that is sensitive to the touch of a user input object (e.g., a finger or a stylus). The touch-sensitive component may serve to implement a virtual keyboard. Other example user input components include a microphone, a traditional keyboard, cursor-device, joystick, or other devices by which a user may provide user input.

The computing system 705 may include one or more output components 745. The output components 745 may include hardware and/or software for audibly or visually producing content. For instance, the output components 745 may include one or more speakers, earpieces, headsets, handsets, etc. The output components 745 may include a display device, which may include hardware for displaying a user interface and/or messages for a user. By way of example, the output component 745 may include a display screen, CRT, LCD, plasma screen, touch screen, TV, projector, tablet, and/or other suitable display components.

The server computing system 805 may include one or more computing devices 810. In an embodiment, the server computing system 805 may include or is otherwise implemented by one or more server computing devices. In instances in which the server computing system 805 includes plural server computing devices, such server computing devices may operate according to sequential computing architectures, parallel computing architectures, or some combination thereof.

The server computing system 805 may include a control circuit 815 and a non-transitory computer-readable medium 820, also referred to herein as memory 820. In an embodiment, the control circuit 815 may include one or more processors (e.g., microprocessors), one or more processing cores, a programmable logic circuit (PLC) or a programmable logic/gate array (PLA/PGA), a field programmable gate array (FPGA), an application specific integrated circuit (ASIC), or any other control circuit. In an embodiment, the control circuit 815 may be programmed by one or more computer-readable or computer-executable instructions stored on the non-transitory computer-readable medium 820.

In an embodiment, the non-transitory computer-readable medium 820 may be a memory device, also referred to as a data storage device, which may include an electronic storage device, a magnetic storage device, an optical storage device, an electromagnetic storage device, a semiconductor storage device, or any suitable combination thereof. The non-transitory computer-readable medium may form, e.g., a hard disk drive (HDD), a solid state drive (SDD) or solid state integrated memory, a random access memory (RAM), a read-only memory (ROM), an erasable programmable read-only memory (EPROM or Flash memory), a static random access memory (SRAM), dynamic random access memory (DRAM), a portable compact disc read-only memory (CD-ROM), a digital versatile disk (DVD), and/or a memory stick.

The non-transitory computer-readable medium 820 may store information that may be accessed by the control circuit 815. For instance, the non-transitory computer-readable medium 820 (e.g., memory devices) may store data 825 that may be obtained, received, accessed, written, manipulated, created, and/or stored. The data 825 may include, for instance, any of the data or information described herein. In some implementations, the server system 805 may obtain data from one or more memories that are remote from the server system 805.

The non-transitory computer-readable medium 820 may also store computer-readable instructions 830 that may be executed by the control circuit 815. The instructions 830 may be software written in any suitable programming language or may be implemented in hardware. The instructions may include computer-readable instructions, computer-executable instructions, etc. As described herein, in various embodiments, the terms "computer-readable instructions" and "computer-executable instructions" are used to describe software instructions or computer code configured to carry out various tasks and operations. In various embodiments, if the computer-readable or computer-executable instructions form modules, the term "module" refers broadly to a collection of software instructions or code configured to cause the control circuit 815 to perform one or more functional tasks. The modules and computer-readable/executable instructions may be described as performing various operations or tasks when the control circuit 815 or other hardware component is executing the modules or computer-readable instructions.

The instructions 830 may be executed in logically and/or virtually separate threads on the control circuit 815. For example, the non-transitory computer-readable medium 820 may store instructions 830 that when executed by the control circuit 815 cause the control circuit 815 to perform any of the operations, methods and/or processes described herein. In some cases, the non-transitory computer-readable medium 820 may store computer-executable instructions or computer-readable instructions, such as instructions to perform at least a portion of the methods of FIGS. 6A-6D.

The server computing system 805 may include one or more communication interfaces 835. The communication interfaces 835 may be used to communicate with one or more other systems. The communication interfaces 835 may include any circuits, components, software, etc. for communicating via one or more networks (e.g., networks 750). In some implementations, the communication interfaces 835 may include for example, one or more of a communications controller, receiver, transceiver, transmitter, port, conductors, software and/or hardware for communicating data/information.

The computing system 705 and/or the server computing system 805 may also be in communication with a user device 905 that is communicatively coupled over the networks 750. The user device 905 may include one or more computing devices 910.

The user device 905 may include a control circuit 915 and a non-transitory computer-readable medium 920, also referred to herein as memory 920. In an embodiment, the control circuit 915 may include one or more processors (e.g., microprocessors), one or more processing cores, a programmable logic circuit (PLC) or a programmable logic/gate array (PLA/PGA), a field programmable gate array (FPGA), an application specific integrated circuit (ASIC), or any other control circuit. In an embodiment, the control circuit 915 may be programmed by one or more computer-readable or computer-executable instructions stored on the non-transitory computer-readable medium 920.

In an embodiment, the non-transitory computer-readable medium 920 may be a memory device, also referred to as a data storage device, which may include an electronic storage device, a magnetic storage device, an optical storage device, an electromagnetic storage device, a semiconductor storage device, or any suitable combination thereof. The non-transitory computer-readable medium may form, e.g., a hard disk drive (HDD), a solid state drive (SDD) or solid state integrated memory, a random access memory (RAM), a read-only memory (ROM), an erasable programmable read-only memory (EPROM or Flash memory), a static random access memory (SRAM), dynamic random access memory (DRAM), a portable compact disc read-only memory (CD-ROM), a digital versatile disk (DVD), and/or a memory stick.

The non-transitory computer-readable medium 920 may store information that may be accessed by the control circuit 915. For instance, the non-transitory computer-readable medium 920 (e.g., memory devices) may store data 925 that may be obtained, received, accessed, written, manipulated, created, and/or stored. The data 925 may include, for instance, any of the data or information described herein. In some implementations, the user device 905 may obtain data from one or more memories that are remote from the user device 905.

The non-transitory computer-readable medium 920 may also store computer-readable instructions 930 that may be executed by the control circuit 915. The instructions 930 may be software written in any suitable programming language or may be implemented in hardware. The instructions may include computer-readable instructions, computer-executable instructions, etc. As described herein, in various embodiments, the terms "computer-readable instructions" and "computer-executable instructions" are used to describe software instructions or computer code configured to carry out various tasks and operations. In various embodiments, if the computer-readable or computer-executable instructions form modules, the term "module" refers broadly to a collection of software instructions or code configured to cause the control circuit 915 to perform one or more functional tasks. The modules and computer-readable/executable instructions may be described as performing various operations or tasks when the control circuit 915 or other hardware component is executing the modules or computer-readable instructions.

The instructions 930 may be executed in logically or virtually separate threads on the control circuit 915. For example, the non-transitory computer-readable medium 920 may store instructions 930 that when executed by the control circuit 915 cause the control circuit 915 to perform any of the operations, methods and/or processes described herein. In some cases, the non-transitory computer-readable medium 920 may store computer-executable instructions or computer-readable instructions, such as instructions to perform at least a portion of the methods of FIGS. 6A-6D.

The user device 905 may also include one or more user input components 935 that receives user input. For example, the user input component 935 may be a touch-sensitive component (e.g., a touch-sensitive display screen or a touch pad) that is sensitive to the touch of a user input object (e.g., a finger or a stylus). The touch-sensitive component may serve to implement a virtual keyboard. Other example user input components include a microphone, a traditional keyboard, cursor-device, joystick, or other devices by which a user may provide user input.

The user device 905 may include one or more output components 940. The output components 940 may include hardware and/or software for audibly or visually producing content. For instance, the output components 940 may include one or more speakers, earpieces, headsets, handsets, etc. The output components 940 may include a display device, which may include hardware for displaying a user interface and/or messages for a user. By way of example, the output component 940 may include a display screen, CRT, LCD, plasma screen, touch screen, TV, projector, tablet, and/or other suitable display components.

The user device 905 may include one or more communication interfaces 945. The communication interfaces 945 may be used to communicate with one or more other systems. The communication interfaces 945 may include any circuits, components, software, etc. for communicating via one or more networks (e.g., networks 750). In some implementations, the communication interfaces 945 may include for example, one or more of a communications controller, receiver, transceiver, transmitter, port, conductors, software and/or hardware for communicating data/information.

The one or more networks 750 may be any type of communications network, such as a local area network (e.g., intranet), wide area network (e.g., Internet), or some combination thereof and may include any number of wired or wireless links. In general, communication over a network 750 may be carried via any type of wired and/or wireless connection, using a wide variety of communication protocols (e.g., TCP/IP. HTTP. SMTP, FTP), encodings or formats (e.g., HTML, XML), and/or protection schemes (e.g., VPN, secure HTTP. SSL).

Additional Discussion of Various Embodiments

Embodiment 1 relates to a computing system. The computing system may include a control circuit configured to perform operations. The operations may include receiving data indicating an inertial state of a vehicle, simulating a fluid based on the data indicating the inertial state of the vehicle, and outputting command instructions to cause the simulated fluid to be visualized within an interior of the vehicle using one or more lighting elements from among a plurality of activatable lighting elements of the vehicle.

Embodiment 2 includes the computing system of Embodiment 1. In this embodiment, the control circuit is configured to model fluid dynamics associated with the fluid based on the data indicating the inertial state of the vehicle to simulate the fluid based on the data indicating the inertial state of the vehicle.

Embodiment 3 includes the computing system of one of Embodiment 1 or 2. In this embodiment, the control circuit is configured to determine the one or more lighting elements from among the plurality of activatable lighting elements to be selectively deactivated, activated, or both, to simulate the fluid based on the data indicating the inertial state of the vehicle.

Embodiment 4 includes the computing system of any one of Embodiments 1 through 3. In this embodiment, to output the command instructions to cause the simulated fluid to be visualized within the interior of the vehicle the control circuit is configured to output the command instructions to activate, deactivate, or both, the one or more lighting elements from among the plurality of activatable lighting elements to visualize the simulated fluid within the interior of the vehicle.

Embodiment 5 includes the computing system of any one of Embodiments 1 through 4. In this embodiment, the control circuit is further configured to receive a first input to execute a motion sickness mitigation application; in response to executing the motion sickness mitigation application, receive a second input identifying a respective location of one or more occupants within the vehicle or a zone within the vehicle; and determine the one or more lighting elements from among the plurality of activatable lighting elements to visualize the simulated fluid based on the second input.

Embodiment 6 includes the computing system of any one of Embodiments 1 through 5. In this embodiment, the control circuit is further configured to: receive data indicating a location of an occupant within the vehicle; and determine the one or more lighting elements from among the plurality of activatable lighting elements to visualize the simulated fluid based on the location of the occupant such that the visualization of the simulated fluid is in a field of view of the occupant.

Embodiment 7 includes the computing system of any one of Embodiments 1 through 6. In this embodiment, the plurality of activatable lighting elements are provided at, at least one of: (i) a dashboard of the vehicle, (ii) one or more seats of the vehicle, (iii) one or more door panels of the vehicle. (iv) one or more display screens of the vehicle, (v) one or more windows of the vehicle, or (vi) one or more consoles of the vehicle.

Embodiment 8 includes the computing system of any one of Embodiments 1 through 7. In this embodiment, the plurality of activatable lighting elements are provided in an array, and the command instructions are configured to deactivate, activate, or both, the one or more lighting elements of the plurality of activatable lighting elements provided in the array to visualize the simulated fluid.

Embodiment 9 includes the computing system of any one of Embodiments 1 through 8. In this embodiment, the control circuit is further configured to: determine at least one of the linear acceleration or the angular velocity of the vehicle based on the data indicating the inertial state of the vehicle, and simulate the fluid based on at least one of the linear acceleration or the angular velocity of the vehicle.

Embodiment 10 includes the computing system of any one of Embodiments 1 through 9. In this embodiment, to simulate the fluid the control circuit is configured to determine movement of suspended air bubbles in the fluid based on the data indicating the inertial state of the vehicle, and the command instructions are configured to cause the one or more lighting elements from among the plurality of activatable lighting elements to be controlled to visualize the movement of the suspended air bubbles in the fluid based on the inertial state of the vehicle.

Embodiment 11 includes the computing system of any one of Embodiments 1 through 10. In this embodiment, as the vehicle turns in a first direction, the command instructions are configured to deactivate, activate, or both, a first subset of the plurality of activatable lighting elements to visualize the simulated fluid, based on how a linear velocity and angular orientation of the vehicle changes over time based on the inertial state, and as the vehicle turns in a second direction, the command instructions are configured to deactivate, activate, or both, a second subset of the plurality of activatable lighting elements to visualize the simulated fluid, based on how the linear velocity and angular orientation of the vehicle changes over time based on the inertial state.

Embodiment 12 includes the computing system of any one of Embodiments 1 through 11. In this embodiment, the control circuit is configured to receive the data indicating the inertial state of the vehicle from at least one of: (i) one or more accelerometers, (ii) one or more gyroscopes, (iii) one or more magnetometers, (iv) one or more inclinometers, (v) one or more cameras, (vi) one or more LIDAR sensors, (vii) one or more RADAR sensors, (viii) one or more wheel speed sensors, or (ix) one or more global navigation positioning sensors.

Embodiment 13 includes the computing system of any one of Embodiments 1 through 12. In this embodiment, the data indicating the inertial state of the vehicle comprises at least one of: (i) acceleration data of the vehicle, (ii) angular motion data of the vehicle, (iii) speed data of the vehicle, (iv) pitch angle data of the vehicle, (v) roll angle data of the vehicle, or (vi) yaw angle data of the vehicle.

Embodiment 14 includes the computing system of any one of Embodiments 2 through 13. In this embodiment, the control circuit is configured to: determine, based on a default setting or a user setting, a viscosity of the fluid to model the fluid dynamics associated with the fluid, and wherein the simulated fluid is based on the viscosity of the fluid.

Embodiment 15 includes the computing system of any one of Embodiments 1 through 14. In this embodiment, the simulated fluid comprises a simulation of the fluid itself and a simulation of one or more objects in the fluid, the one or more objects comprising one or more of: (i) granules, (ii) air bubbles, (iii) filaments, or (iv) fiber-like structures.

Embodiment 16 relates to a computer-implemented method. The computer-implemented method may include receiving data indicating an inertial state of a vehicle; simulating a fluid based on the data indicating the inertial state of the vehicle; and outputting command instructions to cause the simulated fluid to be visualized within an interior of the vehicle using one or more lighting elements from among a plurality of activatable lighting elements of the vehicle.

Embodiment 17 includes the computer-implemented method of Embodiment 16. In this embodiment, simulating the fluid based on the data indicating the inertial state of the vehicle comprises modeling fluid dynamics associated with the fluid and one or more objects in the fluid according to the inertial state of the vehicle.

Embodiment 18 includes the computer-implemented method of one of Embodiment 16 or 17. In this embodiment, the vehicle is an autonomous vehicle.

Embodiment 19 includes the computer-implemented method of any one of Embodiments 16 through 18. In this embodiment, simulating the fluid based on the data indicating the inertial state of the vehicle comprises: determining the one or more lighting elements from among the plurality of activatable lighting elements to be selectively deactivated, activated, or both based on at least one of a location of an occupant within the vehicle or based on a viewing direction of the occupant.

Embodiment 20 relates to one or more non-transitory computer-readable media that store instructions that are executable by a control circuit. The instructions, when executed, may cause the control circuit to perform operations. The operations may include receiving data indicating an inertial state of a vehicle; simulating a fluid based on the data indicating the inertial state of the vehicle; and outputting command instructions to cause the simulated fluid to be visualized within an interior of the vehicle using one or more lighting elements from among a plurality of activatable lighting elements of the vehicle.

Additional Disclosure

As used herein, adjectives and their possessive forms are intended to be used interchangeably unless apparent otherwise from the context and/or expressly indicated. For instance, "component of a/the vehicle" may be used interchangeably with "vehicle component" where appropriate. Similarly, words, phrases, and other disclosure herein is intended to cover obvious variants and synonyms even if such variants and synonyms are not explicitly listed.

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein may be implemented using a single device or component or multiple devices or components working in combination. Databases and applications may be implemented on a single system or distributed across multiple systems. Distributed components may operate sequentially or in parallel.

While the subject matter has been described in detail with respect to various specific example embodiments thereof, each example is provided by way of explanation, not limitation of the disclosure. Those skilled in the art, upon attaining an understanding of the foregoing, may readily produce alterations to, variations of, and equivalents to such embodiments. Accordingly, the subject disclosure does not preclude inclusion of such modifications, variations and/or additions to the subject matter as would be readily apparent to one of ordinary skill in the art. For instance, features illustrated or described as part of one embodiment may be used with another embodiment to yield a still further embodiment. Thus, it is intended that the disclosure cover such alterations, variations, and equivalents.

Aspects of the disclosure have been described in terms of illustrative implementations thereof. Numerous other implementations, modifications, or variations within the scope and spirit of the appended claims may occur to persons of ordinary skill in the art from a review of this disclosure. Any and all features in the following claims may be combined or rearranged in any way possible. Accordingly, the scope of the disclosure is by way of example rather than by way of limitation, and the subject disclosure does not preclude inclusion of such modifications, variations or additions to the subject matter as would be readily apparent to one of ordinary skill in the art. Moreover, terms are described herein using lists of example elements joined by conjunctions such as "and," "or," "but," etc. It should be understood that such conjunctions are provided for explanatory purposes only. The term "or" and "and/or" may be used interchangeably herein. Lists joined by a particular conjunction such as "or," for example, may refer to "at least one of" or "any combination of" example elements listed therein, with "or" being understood as "or" unless otherwise indicated. Also, terms such as "based on" should be understood as "based at least in part on."

Those of ordinary skill in the art, using the disclosures provided herein, will understand that the elements of any of the claims, operations, or processes discussed herein may be adapted, rearranged, expanded, omitted, combined, or modified in various ways without deviating from the scope of the disclosure. At times, elements may be listed in the specification or claims using a letter reference for exemplary illustrated purposes and is not meant to be limiting. Letter references, if used, do not imply a particular order of operations or a particular importance of the listed elements. For instance, letter identifiers such as (a), (b), (c), . . . , (i), (ii), (iii), . . . , etc. may be used to illustrate operations or different elements in a list. Such identifiers are provided for the ease of the reader and do not denote a particular order, importance, or priority of steps, operations, or elements. For instance, an operation illustrated by a list identifier of (a), (i), etc. may be performed before, after, or in parallel with another operation illustrated by a list identifier of (b), (ii), etc.

What is claimed is:

1. A computing system, comprising:
a control circuit configured to:
receive data indicating an inertial state of a vehicle;
simulate a fluid based on the data indicating the inertial state of the vehicle; and
output command instructions to cause the simulated fluid to be visualized within an interior of the vehicle using one or more lighting elements from among a plurality of activatable lighting elements of the vehicle,
wherein the simulated fluid comprises a simulation of the fluid itself and a simulation of one or more objects in the fluid, the one or more objects comprising one or more of: (i) granules, (ii) air bubbles, (iii) filaments, or (iv) fiber-like structures.

2. The computing system of claim 1, wherein the control circuit is configured to model fluid dynamics associated with the fluid based on the data indicating the inertial state of the vehicle to simulate the fluid based on the data indicating the inertial state of the vehicle.

3. The computing system of claim 2, wherein the control circuit is configured to:
determine, based on a default setting or a user setting, a viscosity of the fluid to model the fluid dynamics associated with the fluid, and
wherein the simulated fluid is based on the viscosity of the fluid.

4. The computing system of claim 1, wherein the control circuit is configured to determine the one or more lighting elements from among the plurality of activatable lighting elements to be selectively deactivated, activated, or both, to simulate the fluid based on the data indicating the inertial state of the vehicle.

5. The computing system of claim 1, wherein to output the command instructions to cause the simulated fluid to be visualized within the interior of the vehicle the control circuit is configured to:
output the command instructions to activate, deactivate, or both, the one or more lighting elements from among the plurality of activatable lighting elements to visualize the simulated fluid within the interior of the vehicle.

6. The computing system of claim 1, wherein the control circuit is further configured to:
receive a first input to execute a motion sickness mitigation application;
in response to executing the motion sickness mitigation application, receive a second input identifying a respective location of one or more occupants within the vehicle or a zone within the vehicle; and
determine the one or more lighting elements from among the plurality of activatable lighting elements to visualize the simulated fluid based on the second input.

7. The computing system of claim 1, wherein the control circuit is further configured to:
receive data indicating a location of an occupant within the vehicle; and
determine the one or more lighting elements from among the plurality of activatable lighting elements to visualize the simulated fluid based on the location of the occupant such that the visualization of the simulated fluid is in a field of view of the occupant.

8. The computing system of claim 1, wherein the plurality of activatable lighting elements are provided at, at least one of: (i) a dashboard of the vehicle, (ii) one or more seats of the vehicle, (iii) one or more door panels of the vehicle, (iv) one or more display screens of the vehicle, (v) one or more windows of the vehicle, or (vi) one or more consoles of the vehicle.

9. The computing system of claim 1, wherein
the plurality of activatable lighting elements are provided in an array, and
the command instructions are configured to deactivate, activate, or both, the one or more lighting elements of the plurality of activatable lighting elements provided in the array to visualize the simulated fluid.

10. The computing system of claim 1, wherein the control circuit is further configured to:
determine at least one of a liner acceleration or an angular velocity of the vehicle based on the data indicating the inertial state of the vehicle, and
simulate the fluid based on at least one of the linear acceleration or the angular velocity of the vehicle.

11. The computing system of claim 1, wherein
to simulate the fluid the control circuit is configured to determine movement of suspended air bubbles in the fluid based on the data indicating the inertial state of the vehicle, and
the command instructions are configured to cause the one or more lighting elements from among the plurality of activatable lighting elements to be controlled to visualize the movement of the suspended air bubbles in the fluid based on the inertial state of the vehicle.

12. The computing system of claim 1, wherein
as the vehicle turns in a first direction, the command instructions are configured to deactivate, activate, or both, a first subset of the plurality of activatable lighting elements to visualize the simulated fluid, based on how a linear velocity and angular orientation of the vehicle changes over time based on the inertial state, and
as the vehicle turns in a second direction, the command instructions are configured to deactivate, activate, or both, a second subset of the plurality of activatable lighting elements to visualize the simulated fluid, based on how the linear velocity and angular orientation of the vehicle changes over time based on the inertial state.

13. The computing system of claim 1, wherein the control circuit is configured to receive the data indicating the inertial state of the vehicle from at least one of: (i) one or more accelerometers, (ii) one or more gyroscopes, (iii) one or more magnetometers, (iv) one or more inclinometers, (v) one or more cameras, (vi) one or more LIDAR sensors, (vii)

one or more RADAR sensors, (viii) one or more wheel speed sensors, or (ix) one or more global navigation positioning sensors.

14. The computing system of claim 1, wherein the data indicating the inertial state of the vehicle comprises at least one of: (i) acceleration data of the vehicle, (ii) angular motion data of the vehicle, (iii) speed data of the vehicle, (iv) pitch angle data of the vehicle, (v) roll angle data of the vehicle, or (vi) yaw angle data of the vehicle.

15. A computer-implemented method, comprising:
receiving data indicating an inertial state of a vehicle;
simulating a fluid based on the data indicating the inertial state of the vehicle; and
outputting command instructions to cause the simulated fluid to be visualized within an interior of the vehicle using one or more lighting elements from among a plurality of activatable lighting elements of the vehicle,
wherein simulating the fluid based on the data indicating the inertial state of the vehicle comprises modeling fluid dynamics associated with the fluid and one or more objects in the fluid according to the inertial state of the vehicle.

16. The computer-implemented method of claim 15, wherein the vehicle is an autonomous vehicle.

17. The computer-implemented method of claim 15, wherein simulating the fluid based on the data indicating the inertial state of the vehicle comprises:
determining the one or more lighting elements from among the plurality of activatable lighting elements to be selectively deactivated, activated, or both based on at least one of a location of an occupant within the vehicle or based on a viewing direction of the occupant.

18. One or more non-transitory computer-readable media that store instructions that are executable by a control circuit to:
receive data indicating an inertial state of a vehicle;
simulate a fluid based on the data indicating the inertial state of the vehicle; and
output command instructions to cause the simulated fluid to be visualized within an interior of the vehicle using one or more lighting elements from among a plurality of activatable lighting elements of the vehicle,
wherein the simulated fluid comprises a simulation of the fluid itself and a simulation of one or more objects in the fluid, the one or more objects comprising one or more of: (i) granules, (ii) air bubbles, (iii) filaments, or (iv) fiber-like structures.

\* \* \* \* \*